(12) United States Patent
Tovar et al.

(10) Patent No.: US 10,745,660 B2
(45) Date of Patent: Aug. 18, 2020

(54) SYSTEM FOR INCUBATING MICROFLUIDIC DROPLETS AND METHOD FOR PRODUCING HOMOGENEOUS INCUBATION CONDITIONS IN A DROPLET INCUBATION UNIT

(71) Applicant: Leibniz-Institut für Naturstoff-Forschung und Infektionsbiologie—Hans-Knöll-Institut, Jena (DE)

(72) Inventors: Miguel Tovar, Jena (DE); Lisa Mahler, Jena (DE); Emerson Zang, München (DE); Martin Roth, Jena (DE)

(73) Assignee: LEIBNIZ-INSTITUT FUR NATURSTOFF-FORSCHUNG UND INFEKTIONSBIOLOGIE—HANS-KNÖLL-INSTITUT, Jena (DE)

( * ) Notice: Subject to any disclaimer, the term of this patent is extended or adjusted under 35 U.S.C. 154(b) by 49 days.

(21) Appl. No.: 14/937,197

(22) Filed: Nov. 10, 2015

(65) Prior Publication Data

US 2016/0102280 A1 Apr. 14, 2016

(30) Foreign Application Priority Data

Nov. 10, 2014 (DE) .......................... 10 2014 116 360
May 4, 2015 (DE) .......................... 10 2015 106 870

(51) Int. Cl.
| | |
|---|---|
| *B01L 3/00* | (2006.01) |
| *C12M 3/06* | (2006.01) |
| *C12M 1/12* | (2006.01) |
| *C12M 1/04* | (2006.01) |
| *C12M 1/34* | (2006.01) |
| *C12M 1/00* | (2006.01) |

(52) U.S. Cl.
CPC ............ *C12M 23/16* (2013.01); *C12M 23/24* (2013.01); *C12M 25/01* (2013.01); *C12M 41/00* (2013.01); *C12M 41/14* (2013.01); *C12M 41/34* (2013.01)

(58) Field of Classification Search
CPC .................. B01L 3/502761; B01L 2200/0684
See application file for complete search history.

(56) References Cited

U.S. PATENT DOCUMENTS

| | | |
|---|---|---|
| 5,515,466 A | 5/1996 | Lee |
| 5,638,474 A | 6/1997 | Lampert et al. |

(Continued)

FOREIGN PATENT DOCUMENTS

| | | |
|---|---|---|
| EP | 1 425 384 B1 | 6/2004 |
| WO | WO 2004/088314 A1 | 10/2004 |

(Continued)

OTHER PUBLICATIONS

Köster, et al. 2008 "Drop-based microfluidic devices for encapsulation of single cells" *Lab Chip* 8: 1110-1115.

(Continued)

*Primary Examiner* — Natalia Levkovich
(74) *Attorney, Agent, or Firm* — Knobbe, Martens, Olson & Bear, LLP

(57) ABSTRACT

A system for incubating microfluidic droplets includes a droplet incubator, a gas exchanger and a conveyor. A method provides homogeneous incubation conditions in a droplet incubator by targeted introduction of gases and/or gas mixtures into a carrier fluid.

20 Claims, 12 Drawing Sheets

(56) References Cited

U.S. PATENT DOCUMENTS

| | | | |
|---|---|---|---|
| 6,326,203 B1 * | 12/2001 | Worden | C12M 23/06 |
| | | | 210/635 |
| 8,277,757 B2 | 10/2012 | Kelly et al. | |
| 2008/0009027 A1 | 1/2008 | Fraker et al. | |
| 2010/0105112 A1 | 4/2010 | Holtze et al. | |
| 2010/0124759 A1 | 5/2010 | Wang et al. | |
| 2010/0136544 A1 | 6/2010 | Agresti et al. | |
| 2010/0173394 A1 * | 7/2010 | Colston, Jr. | B01F 3/0807 |
| | | | 435/287.2 |
| 2013/0109575 A1 | 5/2013 | Kleinschmidt et al. | |
| 2013/0217601 A1 | 8/2013 | Griffiths et al. | |

FOREIGN PATENT DOCUMENTS

| | | |
|---|---|---|
| WO | WO 2005/097969 A1 | 10/2005 |
| WO | WO 2009/011808 A1 | 1/2009 |
| WO | WO 2009/048673 A2 | 4/2009 |
| WO | WO 2012/103516 A1 | 8/2012 |
| WO | WO 2013/021035 A1 | 2/2013 |
| WO | WO 2013/037938 A1 | 3/2013 |

OTHER PUBLICATIONS

Butler, P.A.G. et al. 1997 "Capillary Electrophoresis Detector Using a Light Emitting Diode and Optical Fibres" *Analyst* 122: 949-953.

Cao, Z. et al. 2013 "Droplet sorting based on the number of encapsulated particles using a solenoid valve" *Lab on a Chip* 13: 171-178.

Leung, S.-A. et al. 2004 "Continuous real-time bubble monitoring in microchannels using refractive index detection" *Meas Sci Technol* 15: 290-296.

Martin, K. et al. 2003 "Generation of larger numbers of separated microbial populations by cultivation in segmented-flow microdevices" *Lab Chip* 3: 202-207.

* cited by examiner

SYSTEM FOR INCUBATING MICROFLUIDIC DROPLETS AND METHOD FOR PRODUCING HOMOGENEOUS INCUBATION CONDITIONS IN A DROPLET INCUBATION UNIT

FIELD OF THE INVENTION

An embodiment of the invention relates to a system for incubating microfluidic droplets, comprising a droplet incubator, a gas exchanger and a conveyor, wherein microfluidic droplets are present in the droplet incubator, and a carrier fluid comprising gas or gas mixtures is continuously led in a circuit. In a further embodiment, the invention relates to a method for providing homogeneous incubation conditions in a droplet incubator by introducing gases or gas mixtures into the carrier fluid. Another embodiment relates to the use of the system, for example, for biological, chemical and/or physical problems such as materials science problems.

BACKGROUND

Droplet-based microfluidics represents an alternative to using the conventional culturing of cells or cell-free systems in microtiter plates. Droplet-based microfluidic systems are characterized by low material consumption, a high throughput and a high sensitivity of the biological, medical or chemical analyses to be conducted. The microfluidic droplets are used as micro-reactors in a femtoliter to nanoliter volume range in numerous different applications.

EP 1 425 384 B1 describes a method for parallel culturing, culturing and analyzing single-cell microbial cultures, wherein nutrient substances, effectors and microbial metabolites are added to a microorganism population having a homogeneous or heterogeneous composition, and then $10^4$ to $10^8$ partial volumes from 0.1 nL to 1 μL are generated from the suspension and the resulting microcultures are incubated. The growth and the metabolic activities of the microcultures are determined using appropriate measurement methods.

WO 2009/048673 A2 relates to a method for culturing bacteria in a microfluidic system inside droplets that allows for detection of substances produced by said bacteria.

In WO 2012/103516 A1 a method is disclosed that allows for the detection of recombinantly produced compounds of cells, which are encapsulated by a hydrogel particle.

S. Köster et al. Lab Chip, 2008, 8, pp. 1110-1115 describes methods and devices for the encapsulation, incubation and manipulation of individual cells in aqueous droplets in a carrier fluid.

WO 2005/097969 A1 describes a microscale bioreactor for the cultivation of cells, which allows for a provision of oxygen to improve the culturing conditions. The system is not suited for the incubation of microfluidic droplets.

US 2008/0009027 A1 discloses an apparatus for the cultivation of cells in which oxygen may be enhanced by means of a gas-permeable membrane. The system is not suited for the incubation of microfluidic droplets.

In WO 2013/021035 A1, a microfluidic device and a method for cell-based assays are described, as is a method for using the microfluidic device for culturing cells. In particular, a "microfluidic apparatus" is claimed which has an area for culturing biological cells as well as a microfluidic channel for transporting a substance, wherein said culturing area and the channel are separated from one another by a wall that is permeable to the substance.

In US 2010/0124759 A1, the use of droplets for culturing and/or examining cells or other species is disclosed, wherein, for example, an examination is conducted to determine how different cell types react in a "microfluidic device" with different active substances, for example, an indicator or carbohydrate components such as sugar structures.

A disadvantage of the prior art is that so far only droplet incubations with greatly limited oxygen supply could be implemented. In addition, it has been found to be challenging to achieve a homogeneous and reproducible cell growth in droplets and to maintain it over long incubation times. An essential reason for this is the absence of homogeneous surrounding conditions with constant availability of the gases or gas mixtures used to a large number of droplets. In particular, concentration differences between the individual droplets with regard to the gases or gas mixtures dissolved in them, particularly oxygen, lead, for example, to inhomogeneities in the growth of cells or the production rates of metabolites. Differences in the surrounding can lead to the undesired formation of different phenotypes within the cells to be examined, whereby the results of a screening carried out based on these cells can become distorted or unusable.

Using the devices and methods available in the prior art, it is not possible to implement applications that require cell multiplication or the survival of cells over a prolonged time period, with reproducible results. Methods have indeed been described that are suitable for providing oxygen within the microfluidic droplets for short time periods. In the process, the high affinity of a carrier fluid for the gaseous oxygen is exploited. However, the disadvantage of this method is that the carrier fluid is not led cyclically through an incubator, and the number of the incubated droplets is seriously limited. As a result, only short incubation times are reached.

An essential technical challenge of droplet-based microfluidics consists in providing defined and reproducible conditions for culturing cells or cell-free systems that comprise isolated cell components or chemical components, for example, instead of viable cells. The production of these defined and reproducible conditions relates particularly to providing a homogeneous useful gas distribution in the microfluidic droplets. The term "useful gas" denotes, for the conceivable, primarily biological, applications of certain embodiments of the invention, the gas that is metabolized, for example, by the cell cultures inside the microfluidic droplets and converted into a waste gas in the process. For most cell cultures, the useful gas is oxygen or an air mixture which contains oxygen. However, such cell cultures, microorganisms or cell-free systems also exist that are preferably supplied with a useful gas that is different from oxygen or an air mixture.

SUMMARY OF THE INVENTION

Based on this prior art, a problem addressed by some embodiments of the present invention consists in providing a system for incubating microfluidic droplets and a method for providing homogeneous incubation conditions in a droplet incubator, which do not have the disadvantages of the methods and systems described in the prior art and which overcome the technical challenges. In particular, these embodiments of the present invention aim to solve the problem of providing a system and a method that ensure a homogeneous useful gas supply and distribution in the microfluidic droplets.

According to such embodiments of the invention, the problem is solved by a system for incubating microfluidic droplets, comprising a droplet incubator, a gas exchanger and a conveyor, wherein, in the droplet incubator, microfluidic droplets are present which contain the cell suspensions and/or dissolved reagents, and the droplet incubator is connected by a flow-through conduit to a gas exchanger, wherein the flow-through conduit form a circuit for a carrier fluid which comprises gas or gas mixtures, and the conveyor leads the carrier fluid continuously through the droplet incubator and the gas exchanger.

In some embodiments, the system further includes a detector configured to determine the oxygen concentration within the microfluidic droplets and the system is configured such that the flow rate of the carrier fluid is adjusted by the conveyor according to the measured oxygen concentration.

DETAILED DESCRIPTION OF CERTAIN EMBODIMENTS

Figure 1:
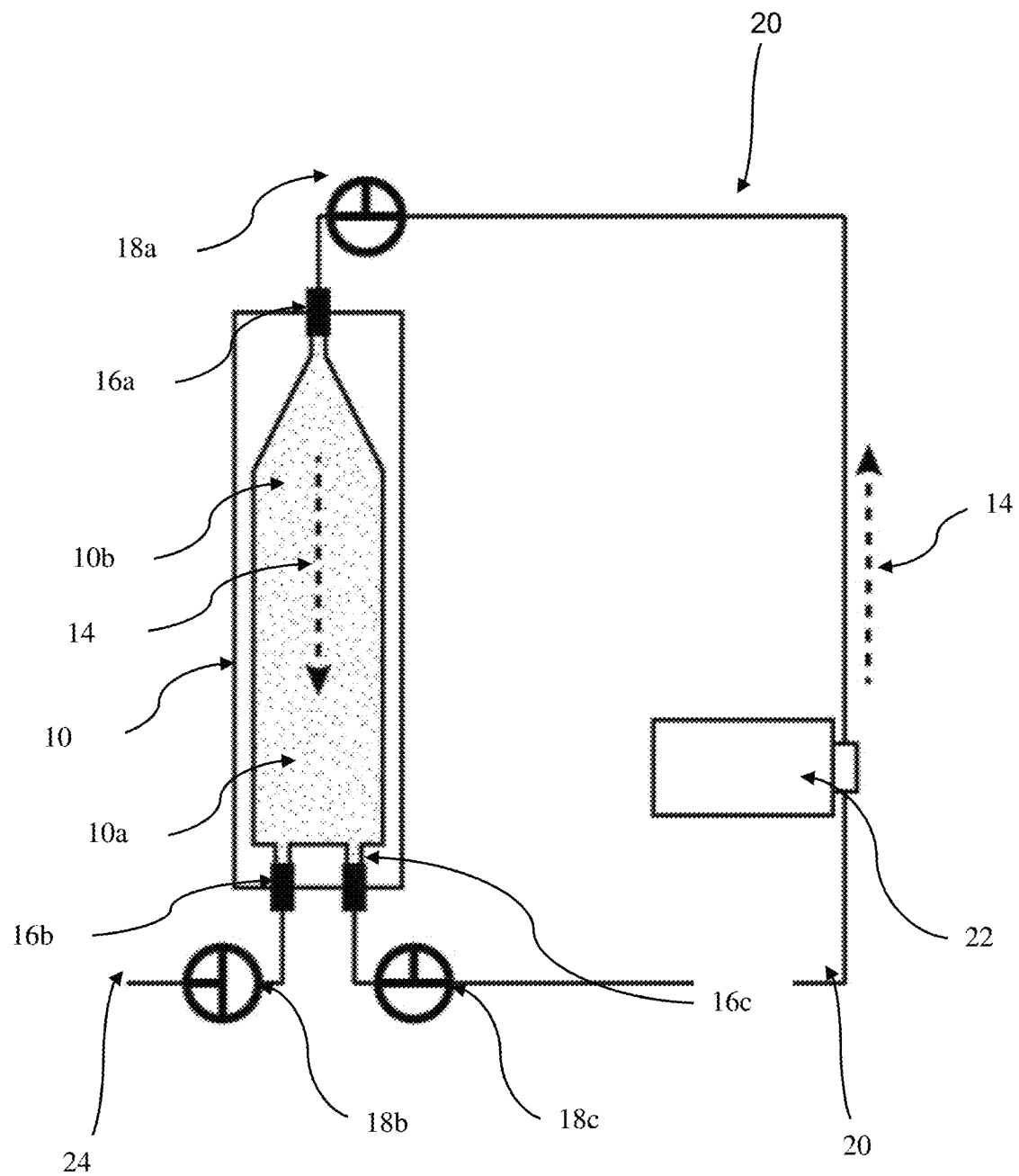
FIG. 1: A representation of a preferred embodiment of the system according to the invention, consisting of droplet incubator (10) and conveyor (22), as well as of a gas exchanger (26) which is formed by the flow-through conduit (20).

Without intending to be limiting, embodiments of the invention are explained in more detail with reference to exemplary embodiments and examples.

Embodiments of the invention lie primarily in the field of biotechnology and preferably relates to the field of cell culturing, which so far has been carried out mainly on microtiter plates or in shaking flasks. In recent years, progressive innovations have been made in the field of two-phase microfluidics towards miniaturization and increased throughput associated with a broad method spectrum for manipulating and/or analyzing the microfluidic droplets, so that droplet-based microfluidics is one of the most modern techniques in the field of ultrahigh throughput screening methods. In particular, the development of surfactants that contribute to droplet stability has influenced this development. The term "droplet-based microfluidics" or "droplet-based microfluidics" describes the preparation of extremely small aqueous droplets, preferably in the picoliter range, in an oily phase, for example, for cell culturing or for preparing cell-free systems. The term "cell-free systems" covers biological, chemical and/or physical applications such as materials science applications, for example.

In general, in the biological context of embodiments of the invention, the term "useful gas" should be understood to cover gases and/or gas mixtures which are provided in order to produce or maintain surrounding conditions that are suitable, for example, for generating and maintaining the surrounding conditions that are needed for the biological materials used or for their metabolic activity, and in which they survive. In the case of chemical or materials science applications of embodiments of the invention, the term "useful gas" is used for gases and/or gas mixtures that allow chemical reactions or their execution or that are used as reactants.

In the context of this invention, the term "microfluidic droplet" refers to an aqueous droplet in an oily phase, wherein the droplet volume is in the femtoliter to nanoliter range. The oily phase is also referred to as carrier fluid in the context of this invention. Microfluidic droplets are characterized particularly in that the droplets and the carrier fluid consist of two different immiscible fluids.

It is preferable to use oxygen-free gas mixtures for applications with cells in the case of anaerobic microorganisms. Furthermore, it is preferable that the microfluidic droplets comprise cell suspensions, dissolved reagents and/or suspended reagents. In the sense of the invention, the term "suspended reagents" preferably describes nanoparticle suspensions, crystal suspensions and/or immobilized chemicals and/or reagents. This means in particular dissolved and/or suspended mixtures.

In the light of the disclosure of the teaching according to the invention, the average person skilled in the art knows that the oxygen in oxygen-free mixtures can be replaced with nitrogen. Furthermore, it is preferable to use rare gases in order to produce anoxic conditions. The average person skilled in the art knows that rare gases are the elements of the 8th main group of the periodic table of the elements. In the context of this invention, rare gas also covers any gas mixture consisting of rare gases.

Additional preferred useful gases are selected from the group comprising hydrogen, carbon dioxide, gas mixtures and/or any conceivable combination of the mentioned gases. Furthermore, it is preferable for the gas mixtures to contain trace amounts of other gases that allow or facilitate the culturing and the providing of homogeneous surrounding conditions. Eukaryotic cells, for example, animal and/or human cells, need, for example, a gas mixture such as an air mixture, which preferably contains oxygen and 5% carbon dioxide.

In the sense of this invention, the term "air" denotes a mixture of gases whose composition substantially resembles the composition of earth's atmosphere, for example, close to the ground. The average person skilled in the art knows what the composition of earth's atmosphere is, for example, close to the ground, and that it contains, in particular, nitrogen, oxygen, carbon dioxide and/or smaller amounts of other gases, particularly rare gases. Earth's atmosphere, whether at the altitude of the ocean surface or, for example, at 1000 m, 3000 m or 7000 m or higher, is also referred to as ambient atmosphere in the sense of this invention. The terms "air" and "air mixture" are used synonymously in the context of this invention.

If algae and/or plant cells are used according to embodiments of the invention, a carbon dioxide gas mixture can be used as useful gas, for example. Nitrogen fixing bacteria are preferably supplied with a nitrogen gas mixture. In the light of the disclosure of the teaching according to the invention, the average person skilled in the art knows which gases or gas mixtures can be used moreover in the system according to the invention, particularly if the system is used for chemical, biological or physical applications, for example, for materials science applications.

The incubation of microfluidic droplets comprises the providing of microfluidic droplets which are present in a carrier fluid. The system according to the invention comprises a droplet incubator. The term "droplet incubator" refers to a device, an apparatus or a system that comprises a container configured for the incubation of microfluidic droplets in a carrier fluid. Different shapes of the container may be suitable for this purpose and the dimension of the container is preferably chosen according to the size of the droplet pool that is to be incubated. It is however preferred that the droplet incubator is a container having a cylindrical design in a first area, and preferably a design forming a cone that tapers to a tip in a second area. It is preferable for the droplet incubator to be arranged vertically, wherein the first area of the droplet incubator preferably faces a stable substrate and has a flat bottom area so that, advantageously, a high stability of the droplet incubator is ensured. In the context of this invention, the first area of the droplet incubator is also referred to as lower area of the droplet incubator. Accordingly, a movement in the "downward" spatial direction is a movement in the direction of the stable substrate on which the droplet incubator can be arranged. In the context of this invention, the second area of the droplet incubator, which has a design in the shape of a cone with tip, is also referred to as the upper area of the droplet incubator. This embodiment of the invention is preferably used when a carrier fluid is used whose density is greater than the density of the aqueous phase which comprises the microfluidic droplets.

For applications in which a carrier fluid is used whose density is lower than the density of the aqueous phase, it is preferable, for correct functioning, that the system is not arranged as in the above description. Accordingly, in this case, it is preferable that the second area, which preferably has a conical design, faces the substrate, while the preferably cylindrical first area points "upward." The flow then enters the droplet incubator through the downward pointing tip of the conically designed second area. In this embodiment, it is advantageously possible to use a carrier fluid whose density is lower than the density of the aqueous phase in which the microfluidic droplets are present. It was entirely surprising that, in this embodiment design of the invention, the microfluidic droplets can be discharged particularly simply and without loss.

Since the density of the microfluidic droplets and of the aqueous phase containing the droplets is preferably lower than the density of the carrier fluid, the microfluidic droplets accumulate in the top of the cone of the second area of the droplet incubator, which tapers to a tip. The cone tip has an opening out of which flow-through conduit lead. In the sense of this embodiment of the invention, the flow-through conduit can be a hose, a pipe or a tube, for example. The average person skilled in the art knows that the term means a hollow cylindrical elongated device that is used for conducting solid, liquid and/or gaseous substances.

It is preferable that the flow-through conduit leading out of the pointed upper opening of the droplet incubator has a valve with which the flow of a substance through the flow-through conduit can be made possible or completely or partially prevented or regulated. The average person skilled in the art is familiar with the known types of valves and knows which valve type is suitable for use in a system according to the invention. The valves used such a system are preferably selected from straight way valves, angle valves, Y-type valves, three-way valves, throttle valves, flow valves, check valves, pinch valves and/or pressure valves, wherein the valves used are preferably actuated manually or actuated by means of an electrical motor, electrically, electromagnetically, or by means of a medium.

The average person skilled in the art knows, in the light of the present disclosure, that the design of the droplet incubator is not strictly limited to the described preferred shaping, and which other design possibilities can be selected in order to achieve best possible results. For example, the gas exchanger can be integrated in the droplet incubator. This is particularly advantageous if a space-saving design of the system is needed. For other applications of a system according to embodiments the invention, a flat design of the droplet incubator can be preferable. In another preferred embodiment form, structures such as partitions can be built into the droplet incubator, which improve the mixing of the droplets.

Furthermore, it is preferable that at least one device component or several device components or the entire system can be hung, or that they have means for hanging. The hanging can occur, for example, on a rack or on a room ceiling. For example, on the at least one device component or on the system, loops, hooks or eyelets can be provided, by means of which the hanging of the components or of the entire system occurs, for example, using ropes, elastic bands, belts or other attachment means. This design is particularly advantageous if the system is to be uncoupled from potential vibrations of the substrate. It was entirely surprising that, due to this preferred design, a particularly space-saving arrangement of a system becomes possible. As a result, the lower components of the system can also be accessed surprisingly simply, so that maintenance and cleaning work can be carried out efficiently.

It is preferable for the droplet incubator to have three openings into which threaded parts can be advantageously inserted. These threaded parts allow the use of microfluidic flow-through conduit also referred to as "fittings" in the sense of this invention, which originate from the field of high performance liquid chromatography. It was entirely surprising that, by providing the droplet incubator with preferably three openings, the supplying of the microfluidic droplets to other examination or screening assemblies becomes possible in a particularly simple and user-friendly manner.

The fittings as counterparts to threaded parts can preferably be screwed into the threaded parts. The average person skilled in the art knows that a "thread" is understood to mean a profiled notching which extends in continuous coil-shaped pattern in a cylindrical wall in a helical line. In the sense of this embodiment of the invention, it is preferable to refer to this notch as thread. The use of a thread advantageously ensures a reliable, stable and surprisingly traction-resistant and moreover fluid-impermeable connection between the flow-through conduit and the droplet incubator.

It has been shown that, in this manner, a flow-through conduit can be attached particularly simply and reversibly to the droplet incubator. Advantageously, the microfluidic droplets can be introduced into and discharged from the droplet incubator through the flow-through conduit. It was entirely surprising that the design tapering to a tip of the droplet incubator in the form of a pointed cone advantageously allows a gentle exit of the microfluidic droplets from the droplet incubator.

Advantageously, due to the difference in density between the aqueous microfluidic droplets and the carrier fluid, the microfluidic droplets collect in the tip of the conical droplet incubator and form a cohesive volume of microfluidic droplets.

For example, if the microfluidic droplets are to be discharged from the droplet incubator for further examinations out of the droplet incubator, through one of the openings located in the bottom of the droplet incubator, into which a flow-through conduit is inserted by means of the threaded part and/or fitting, carrier fluid can be introduced into the droplet incubator. If, at the same time, a valve is opened, which is provided in the flow-through conduit provided out of the pointed opening of the conical upper area of the droplet incubator, the carrier fluid introduced additionally through the lower inlet into the droplet incubator advantageously displaces an equal volume of microfluidic droplets, volume which leaves the droplet incubator through the opening in the cone tip and is received by the flow-through conduit leading to the gas exchanger.

Advantageously, the process of using the system according to certain embodiments of the invention can be described by the following steps:

1. Filling of the droplet incubator with the microfluidic droplets
2. Incubation phase
3. Discharging of the microfluidic droplets from the droplet incubator It is preferable that the droplets, after the discharging, are supplied to a further microfluidic use. This can be, for example, a screening process, analysis and/or synthesis processes, or cell culturing processes or the processing of components of cell-free systems. Ultrahigh throughput screenings are preferable.

In the droplet incubators, microfluidic droplets are present which comprise, for example, cell suspensions, liposomes, nanocapsules and/or dissolved reagents. In the context of this invention, the term "dissolved reagents" denotes, for example, cell-free systems, proteins, enzymes, biological molecule complexes of non-cellular origin, such as, for example, dyes, synthetic antibiotics, nanoparticles, synthetic molecules, complexes consisting, for example, of several biological or chemical components and/or atom groups or atoms. In particular, by using the last-mentioned reagents, the system according to some embodiments of the invention can advantageously also be used in chemical or materials science contexts, for example, for the production of nanoparticles. In the sense of some embodiments this invention, "cell suspensions" can be selected from suspensions of prokaryotic cells and/or eukaryotic cells or cell components. The average person skilled in the art knows that a cell suspension can comprise one or more types of cells optionally together with cell components or fragments. It is also preferable when the microfluidic droplets contain cell-free systems. In the sense of these embodiments of the invention, these cell-free systems can be used preferably for fatty acid synthesis, DNA replication, RNA synthesis, protein synthesis or for transcription or translation systems; naturally it is also possible to carry out this reaction in systems comprising natural or man-made cells.

In the context of this invention, the term "cell culture" or "cell cultures" is used as a generic term for the cell suspensions and dissolved reagents contained in the microfluidic droplets. The term cell suspension here comprises preferably natural or man-made cells such as lipid vesicles, for example.

The average person skilled in the art knows that the term "dissolved" includes reagents that are present, for example, suspended or emulsified or in the form of a solution as a homogeneous mixture in the microfluidic droplets. It can be preferable that the flow-through conduit, which connect the droplet incubator to the gas exchanger and the gas exchanger to the conveyor, form a closed circuit for a carrier fluid, wherein the flow-through conduit themselves form the gas exchanger in a preferred design of the invention.

The carrier fluid is selected from: fluorinated oils, organic oils, in particular oils comprising long carbon chains, silicone oils, oils comprising surfactants, in particular fluorinated amphiphilic surfactants. In the sense of some embodiments of the present invention, a surfactant is a substance that lowers the surface tension of a fluid or the boundary surface tension between two phases. As a result, the formation of emulsions is advantageously made possible and/or promoted. In the sense of embodiments of the invention, fluorinated surfactants are preferably organic surfactant compounds with amphiphilic character, consisting of a hydrophilic component, for example, polyethylene glycol, and a fluorinated hydrophobic component.

The average person skilled in the art knows which additional oils can be considered for use as carrier fluid. Advantageously, fluorinated oils have surprisingly good solubility for gases in connection with a poor solubility for undesired substances. Organic oils are common and as a result they are advantageously easily and readily available.

The carrier fluid comprises gas or gas mixtures in the sense that the gas or gas mixtures are preferably present in enriched form in the carrier fluid. Herein the term "gas exchanger" refers to a device, an apparatus or a system configured to allow the exchange of gas between the carrier fluid and a gas reservoir. To this end the gas exchanger can have different embodiments. It may for instance be preferred that the gas exchanger is a container, which is connected to a gas reservoir. The carrier fluid is transported into said container such that the container is partially filled by the carrier fluid and partially filled by the gas provided by the gas reservoir. It may however also be preferred that the gas exchanger comprises gas permeable flow-through conduits. In this case the transport of the carrier fluid through the gas permeable flow-through conduits allows for a gas exchange between the carrier fluid and the environment, in which the gas permeable flow-through conduits are situated. Herein the gas reservoir for the gas exchange of the carrier fluid can preferably be the air of the room in which the system according to a preferred embodiment is set up.

The conveyor conveys the carrier fluid continuously through the droplet incubator and/or the gas exchanger. In the systems or devices described in the prior art, it is disadvantageous that a gas exchange of the gases or gas mixtures that are present in dissolved form in the carrier fluid with the gases or gas mixtures that are present in the microfluidic droplets occurs only at the boundaries between all of the aqueous droplets that are in close contact and the carrier fluid. As a result, the individual droplets disadvantageously have a different gas exchange depending on their position within the overall volume of the droplets.

Advantageously, in the system according to some embodiments of the invention, two different phase boundaries preferably form, which in each case make a contribution to the surprisingly homogeneous and improved gas supply to the microfluidic droplets. On the one hand, each individual microfluidic droplet preferably has its own phase boundary with respect to the carrier fluid, wherein the droplets are surrounded in particular by the surfactants and/or oil molecules of the carrier fluid. In addition, another phase boundary forms between the cohesive aqueous volume in which the droplets are present, and the carrier fluid. In the context of these embodiments, this phase boundary is preferably referred to as overall phase boundary. It was entirely surprising that, due to the use of these embodiments, the microfluidic droplets are surrounded by a larger amount of carrier fluid. As a result, the gas exchange between droplet and carrier fluid can be improved with surprising quality.

It is preferable for the microfluidic droplets to collect, due to their generally lower density in comparison to the carrier fluid and due to the force of gravity, in the cone tip of the droplet incubator which tapers to a point, wherein these microfluidic droplets are crowded together particularly densely. The transition of the aqueous phase formed by all of the microfluidic droplets to the carrier fluid which generally has a higher density is preferably formed by the overall phase boundary. When the carrier fluid flows through the tip into the droplet incubator with conical design, the microfluidic droplets are swirled and distributed in the carrier fluid which is located in the droplet incubator.

It was entirely surprising that, due to the distribution of the microfluidic droplets in the carrier fluid in the droplet incubator, the carrier fluid flows equally satisfactorily around all the microfluidic droplets. In the carrier fluid, gases or gas mixtures are dissolved, wherein a surprisingly efficient exchange of the gases or gas mixtures dissolved in the carrier fluid with the gases or gas mixtures contained in the microfluidic droplets is made possible.

For culturing, for example, cell suspensions, or for synthesizing dissolved reagents in the microfluidic droplets, the microfluidic droplets need to be supplied with a useful gas. In applications in the biological context, it is preferable that, for example, the cell suspensions and/or the dissolved reagents of this useful gas convert into a waste gas, preferably by biochemical processes such as metabolic processes. In the sense of embodiments of this invention, waste gases are gases which are the products of conversion processes within the cell cultures or microorganisms, or in the dissolved reagents or cell-free systems. They are preferably selected from the group comprising: carbon dioxide, oxygen, hydrogen, methane, hydrogen sulfide, nitrogen and/or any mixture thereof.

If the system according to embodiments of the invention is used, for example, in connection with chemical or physical applications such as, for example, materials science applications, it is possible that, in addition to the mentioned gases and/or gas mixture, other gases or gas mixtures are produced, which are known to the average person skilled in the art. In some applications, it can also be preferable that no waste gas is produced. The term "consumption gas" is used synonymously with the term "waste gas" in the context of embodiments of the present invention.

The waste gas is preferably discharged from the microfluidic droplets and/or replaced with new useful gas. This exchange is advantageously made possible in that newly supplied carrier fluid, which preferably contains unused useful gas, flows cyclically and continuously around the microfluidic droplets present in the droplet incubator in the carrier fluid. Due to the preferred increase in the separation between the droplets and due to the continuous flow of the carrier fluid with the associated movement of the droplets within the droplet incubator, a targeted introduction of useful gases into the microfluidic droplets is made possible. Advantageously, the incubation of the microfluidic droplets is thus made possible under defined and homogeneous conditions.

It was entirely surprising that, as a result of the regular flow around the microfluidic droplets, during growth, the cells contained in the droplets have identical or higher cell densities or metabolite concentrations in comparison to conventional methods for culturing, screening and/or biosynthesis, for example. Advantageously, an increased production of desired metabolites is associated with the increased cell densities, resulting in a simplification of, for example, of subsequent screenings for activity of the biotechnologically relevant compounds. In particular, aerobic growth of the cell cultures becomes possible, by means of which process reactions between the cultures or reagents can be examined, which so far have not been accessible to research because of the inhomogeneous surrounding conditions, particularly in regard to the useful gas supply and/or low metabolite production.

It was entirely surprising that, due to the regular flow around the microfluidic droplets, chemical or physical processes occurring in the droplets have led to an increased product yield or an improved product quality.

Tests have shown that, by means of embodiments of the system according to the invention, five times higher cell densities can be achieved within the microfluidic droplets, in comparison to what was the case before in the prior art in terms of microfluidic applications. In particular, the quantity of the recombinant proteins was increased. In addition, it was entirely surprising that, by using these embodiments, the yield of material could be clearly increased, for example, for further use for purposes of culturing, synthesis and/or screening. This refers to the yield of metabolites, antibodies, DNA and/or RNA, for example.

It was entirely surprising that the results of known screening or culturing methods could also be clearly increased by using the system according to embodiments of the invention, in this case by providing now a homogeneous supply of useful gas to the microfluidic droplets, usually oxygen or a gas mixture comprising oxygen. The finding that an optimization of the useful gas supply is needed in order to optimize the generation of the starting material for screening, culturing and other microfluidic methods, and that this challenge is solved by providing an embodiment of the system according to the invention, in which the carrier fluid is led continuously through the droplet incubator, represents a turning away from the previous technical convention. So far, the professional community had not recognized the providing of a continuous flow of a carrier fluid through the droplet incubator as a means for improving the microfluidic systems known so far.

In particular, by providing continuous flow of the carrier fluid and regular flow of the carrier fluid around the microfluidic droplets, a homogeneous supply of the useful gas to the droplets, for example, a gas or gas mixture which comprises oxygen, is ensured. An inhomogeneous supply with useful gas, which cannot be prevented in the microfluidic systems of the prior art, in the case of the use of the system in biological applications with cell supply, would lead to the formation of different phenotypes, wherein the phenotypes form as a reaction to possibly different surrounding conditions, for example, in terms of gas supply. It is obvious that screening methods that are carried out with different phenotypes of cell cultures can lead to distorted results.

It was completely surprising that this disadvantage of the microfluidic applications described in the prior art, which for the most part based on the fact that no homogeneous useful gas supply is ensured, is overcome by embodiments of the present invention. In particular, nowhere in the prior art is there a description that a droplet incubator is exposed to continuous flow of a carrier fluid through it. Tests have shown that the use of the system according to embodiments of the invention leads to distinguishable differences with regard to the above-mentioned effects between the invention and the methods and devices described in the prior art. However, for certain problems it can also be preferable to adapt embodiments of the system according to the invention so that different phenotypes develop.

An additional advantage of the method according to embodiments of the invention is that the composition of the gases dissolved in the microfluidic droplets can be modulated. By the targeted adaptation of the gas concentration to the specific requirements of the cells to be cultured or cell-free systems, a culturing or synthesis of both aerobic and also anaerobic cultures or reagent solutions is advantageously possible, as are all the transitional forms between these cases.

Moreover, it was entirely surprising that the desired defined and homogeneous incubation conditions can be maintained for time periods from several days to weeks by using embodiments of the system according to the invention.

The system according to embodiments of the invention describes how the device components of the system work together. This cooperation can also be understood as a course of a method.

In another preferred embodiment, embodiments of the invention relate to a system for incubating microfluidic droplets, wherein the gas exchanger comprises a reservoir which is connected to a gas source, and the carrier fluid upon passing through the gas exchanger for the gas exchange resides in the reservoir. For example, the reservoir can be designed as a container in which the carrier fluid having a higher density is located in the lower area and a gas or a gas mixture having lower density than the density of the carrier fluid is located in an upper area.

It is preferable that the gas exchanger is connected by at least two flow-through conduit to the remaining components of the system according to embodiments of the invention. These at least two flow-through means preferably lead from the gas exchanger to the droplet incubator, as well as from the conveyor to the gas exchanger. In addition, a flow-through conduit can be present between the gas exchanger and a gas source, if a gas source is present. It is preferable that the gas source supplies the gas exchanger regularly with unused useful gas. The flow-through conduit which lead from the gas source to the gas exchanger preferably end in the carrier fluid which is present in the lower area of the gas exchanger and which is enriched with the gas or the gas mixture. It is preferable that the gas source is formed by a container which contains the gases or gas mixture. However, it can also be preferable that the gas source is formed by the ambient atmosphere.

In an additional preferred embodiment, embodiments of the invention relate to a system wherein the reservoir is connected, open to gases, to an ambient atmosphere and an air mixture is a component of the gas source.

Furthermore, it is preferable that the flow-through conduit which lead from the gas exchanger to the droplet incubator also end in the carrier fluid which arrives in the droplet incubator by means of the flow-through conduit. In the sense of these embodiments of the invention, the term "end" means that the flow-through conduit preferably protrude into the indicated area and that the ends of the flow-through conduit are preferably present in this area. In the design of the system according to embodiments of the invention that is described here, "end" is understood to mean, for example, that the flow-through conduit protrudes into the carrier fluid and that the gas or gas mixture can arrive in the carrier fluid. The flow of the carrier fluid is propelled by the conveyor. The term "conveyer" refers to a system, a device or an apparatus configured to transport and/or propel carrier fluid through the system. Different embodiments of conveyers are suitable for this purpose. It is preferred that the conveyer comprises a pump. It is particularly preferred that the conveyor is a peristaltic pump. However, it can also be preferable that the conveyor is formed by a device selected from a pressure pump, perfusor syringe, manual pump, piston pump and/or centrifugal pump. The average person skilled in the art knows that, in general, any pump device that is suitable for propelling a fluid can be used in the system according to embodiments of the invention as a conveyer. Tests have shown that, when a peristaltic pump is used, surprisingly regular flow rates and/or speeds of the carrier fluid in the system according to embodiments of the invention can be ensured.

It is further preferred that the conveyer is connected to the gas exchanger by a flow-through means which is filled with carrier fluid and which reaches into the upper area of a reservoir of the gas exchanger which is filled with the gas or gas mixture.

Figure 6:
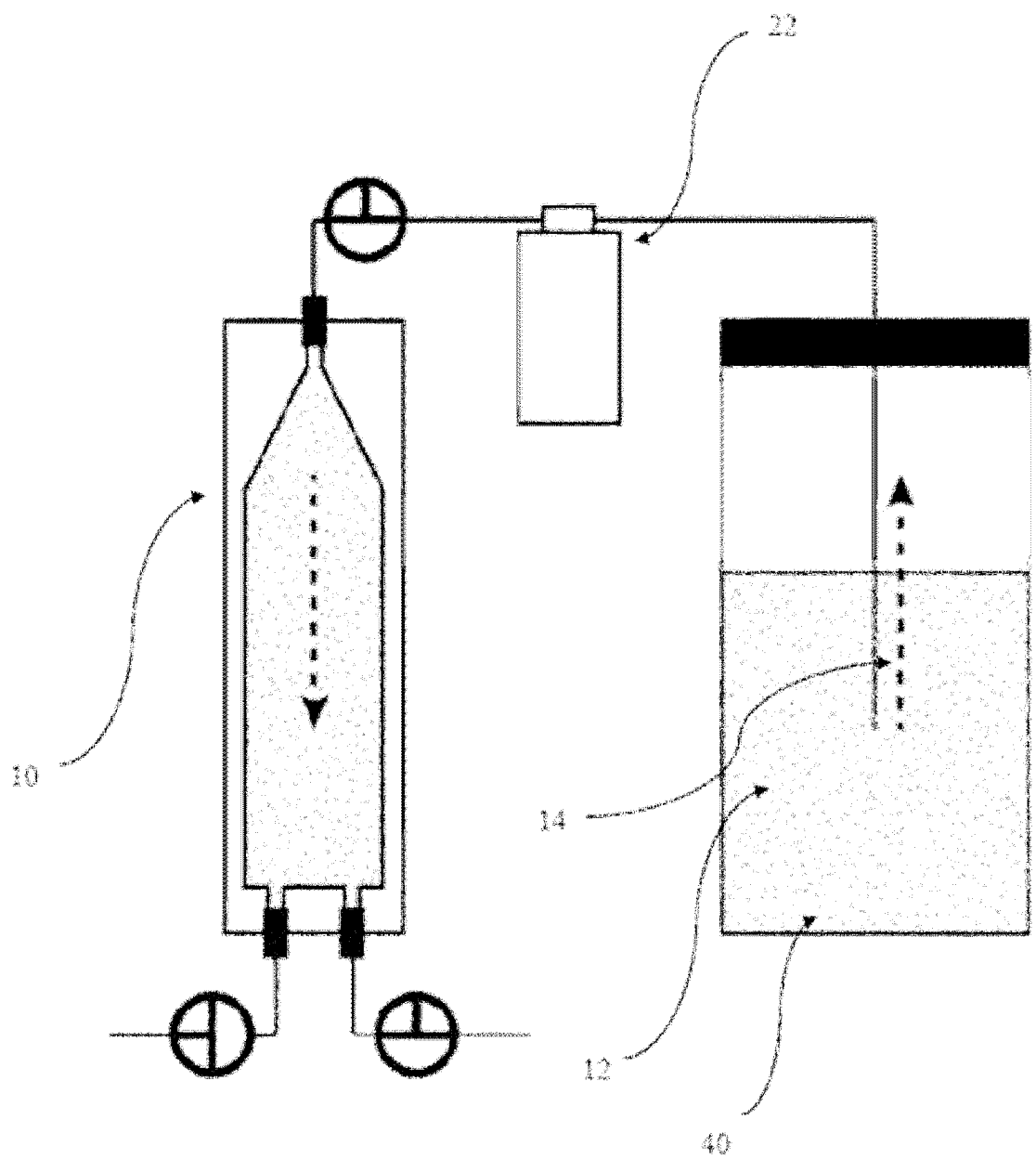
FIG. 6: A representation of a preferred embodiment of a system according to the invention, wherein the gas exchanger (26) is formed by a large container (40) comprising a large amount of carrier fluid (12).
Figure 7:
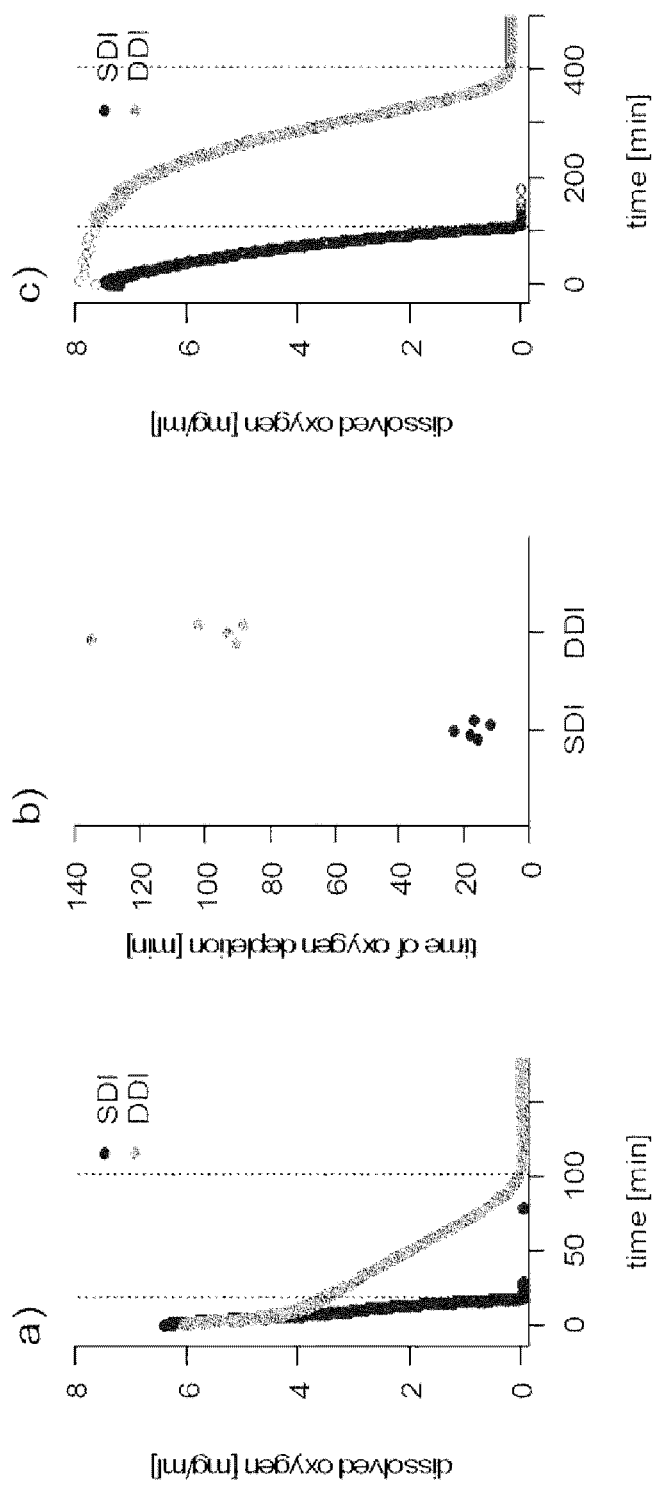
FIG. 7: Experimental data of the dissolved oxygen-concentration (DO) into droplets that have been incubated either with a system known from the prior art denoted static droplet incubation (SDI) or a preferred embodiment of a system according to the invention denoted dynamic droplet incubation (DDI). (a) Shows the dissolved oxygen concentration (DO) over time during DDI and SDI in droplets containing $E.$ $coli$ cells. Droplets were oxygenated prior to the first measurement. Dotted lines mark the time points when the dissolved oxygen concentration falls below the detection limit. (b) Depicts the comparison of time points when the DO reaches the detection limit in five replicate measurements of DO over time. The mean of dissolved oxygen depletion time for SDI (17 min, coefficient of variation (CV) 22.8%) was tested as significantly lower than the mean for DDI (101.3 min, CV 19.1%) with a one sided Welch test ($\alpha=0.05$, p=0.0002319). (c) Shows the depletion of dissolved oxygen in statically and dynamically incubated droplets inoculated with less than 1 cell/droplet in average.
Figure 8:
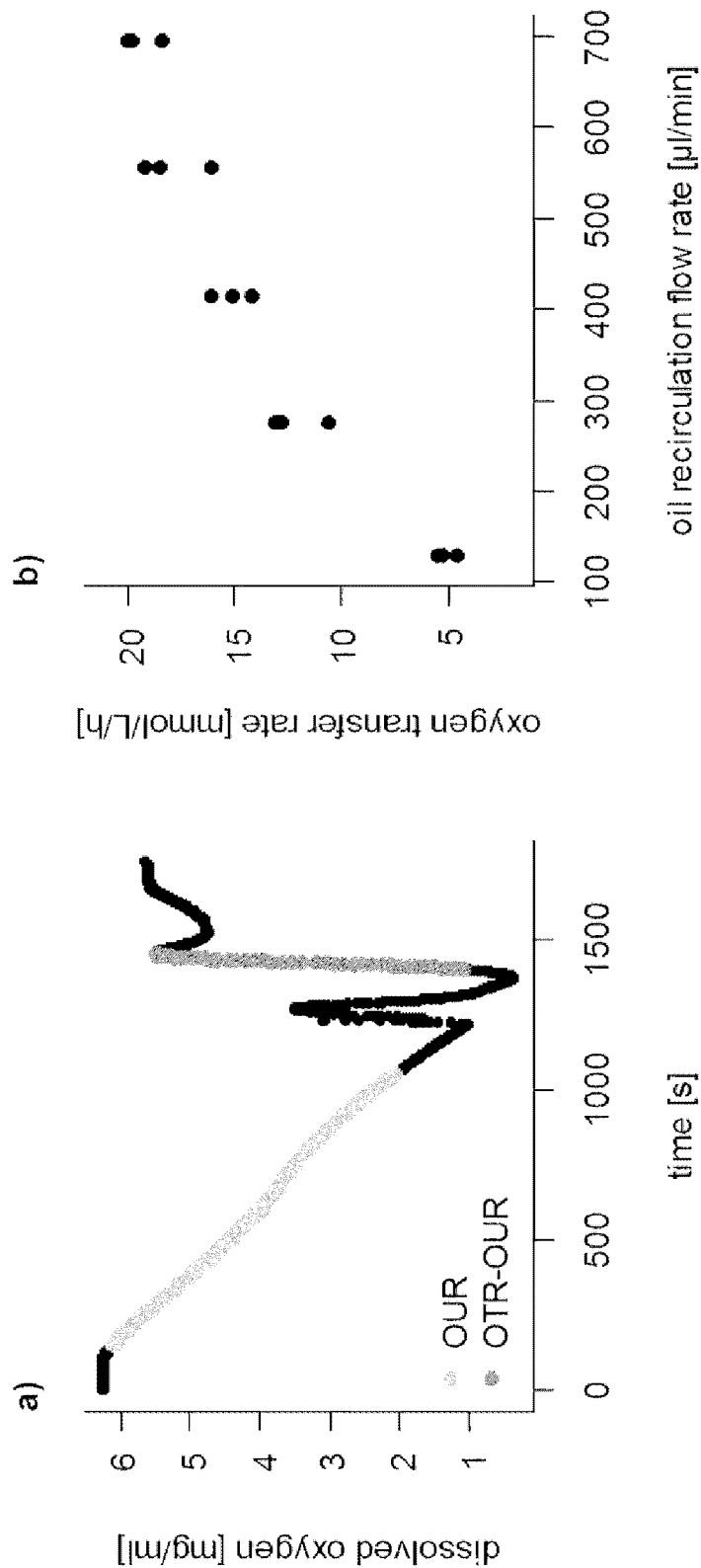
FIG. 8: An estimation of oxygen transfer (OTR) rate by applying a dynamic gassing out method. (a) Dissolved oxygen concentration (DO) over time during dynamic gassing out with droplets containing respiring $E.$ $coli$ cells (oil recirculation speed: 275 μl/min). The light gray part of the graph was recorded after halting carrier oil recirculation. The slope of the decreasing DO was used to estimate the current oxygen uptake rate (OUR). After DO depletion the oil recirculation system was turned on leading to a sudden increase in DO (straight arrow) due to flushing droplets that had direct contact with perfluorinated oil at the bottom of the emulsion bulk through the measurement area of the incubator. During oil recirculation oxygen transfer is enhanced, resulting in an increase in DO (curved arrow), which depends on OTR and OUR and is used to determine the OTR of the system. (b) A depiction of the OTR estimates for five oil recirculation speeds.
Figure 9:
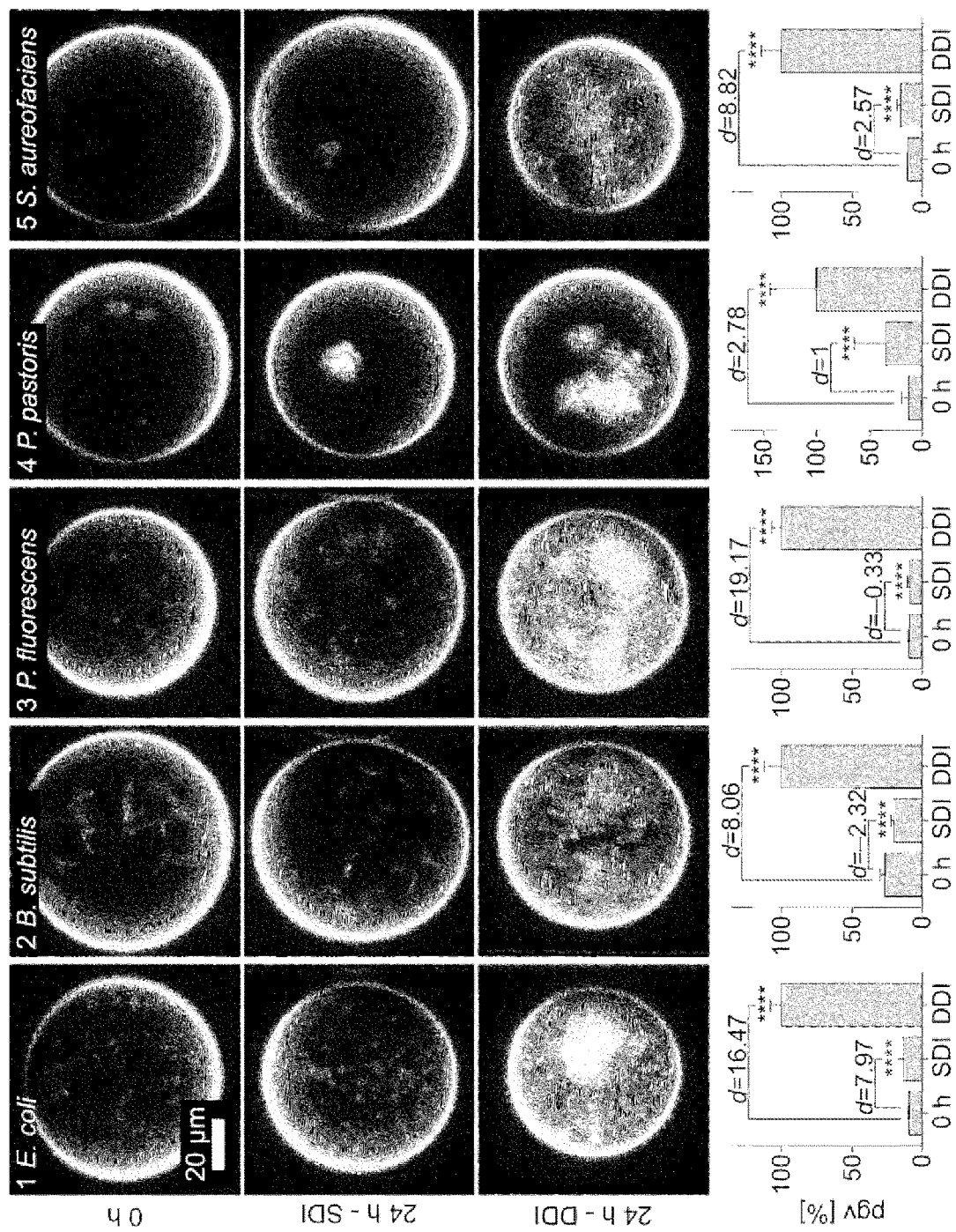
FIG. 9: The biomass yield of different microorganisms in droplets after 24 h (except $S.$ $aureofaciens$—72 h, humid chamber) of DDI and SDI. Population gray values (pgv) were compared with Welch corrected ANOVA and Dunnett's test (both $\alpha=0.05$) in combination with a heteroscedastic consistent covariance estimation, **** significant with p<0.0001. Plotted pgv are standardized to the pgv of the corresponding DDI population. A minimum of 9500 single droplets were analyzed per droplet population. To indicate which effects are practically relevant, the effect size is given using Cohen's d, and 0 h control as reference.
Figure 10:
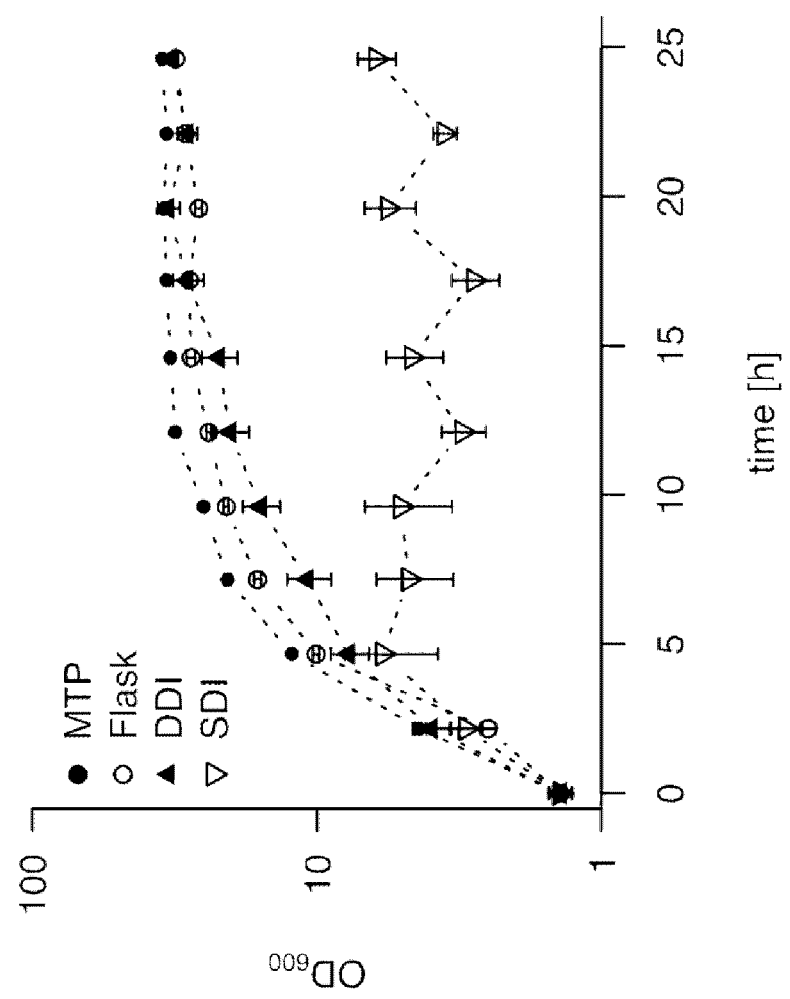
FIG. 10: $E.$ $coli$ growth kinetics in cultures grown in MTP, shaking flask, and in droplets with DDI and SDI. A minimum of 1800 droplets were re-injected and analyzed per time point for SDI and DDI. Gray values were transformed into absorbance values via calibration. Error bars indicate one standard deviation.
Figure 11:
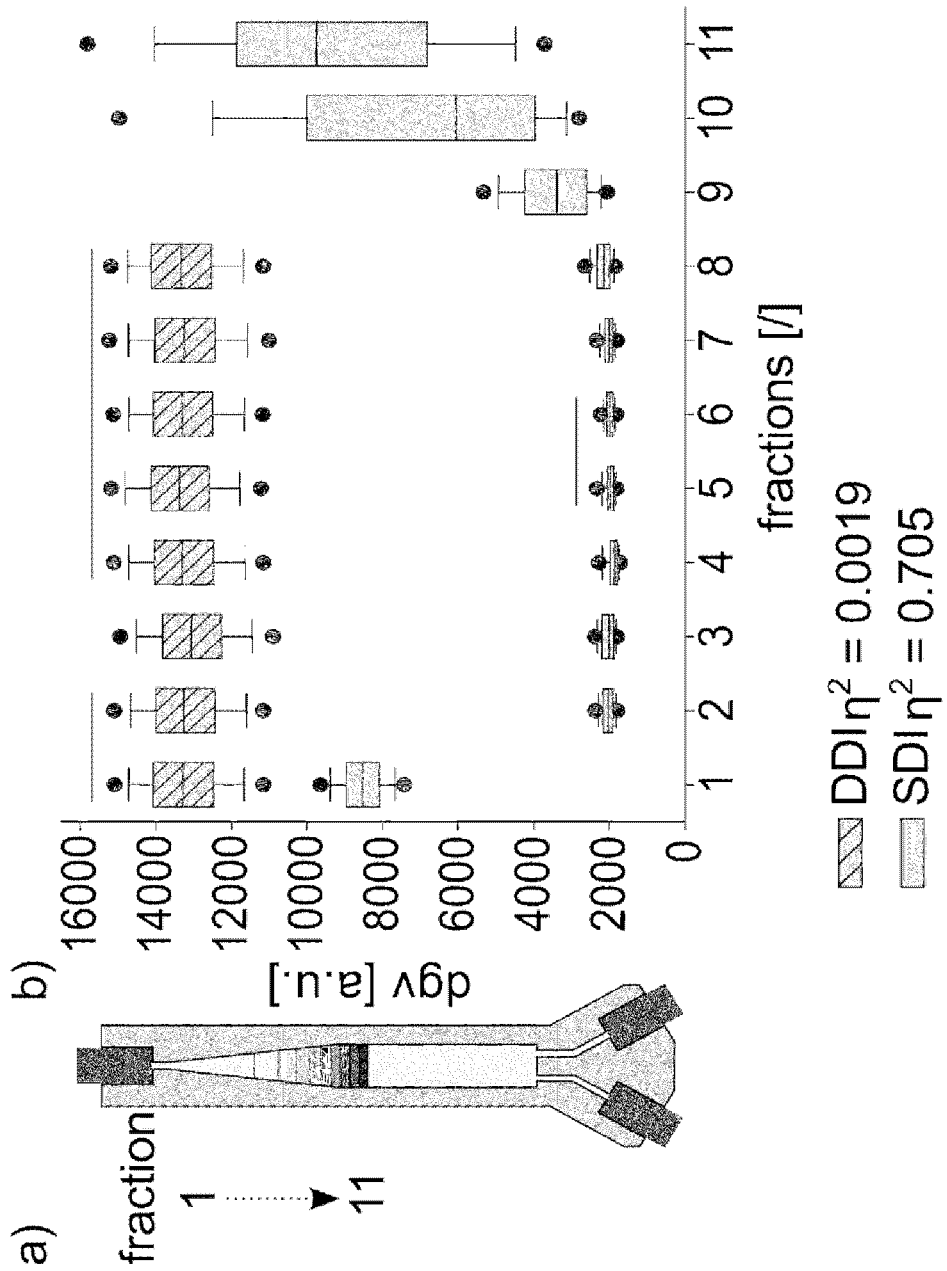
FIG. 11: Data on the inter-droplet variation of growth after droplet incubation. (a) A schematic depiction of re-injected fractions in a droplet population. Each gray layer indicates one fraction of ~150,000 droplets. (b) Droplet population fractions after DDI (hatched) or SDI, with dots representing the 5th and 95th percentiles. Solid lines above boxplots indicate no significant difference between the covered fractions. Means for droplet gray values (dgv) of fractions were compared with Welch corrected ANOVA and Tukey's test (both $\alpha=0.05$) in combination with a heteroscedastic consistent covariance estimation. Cut-off for significance was p<0.05. A minimum of 4500 single droplets were analyzed per fraction. As a measure for effect size $\eta^2$ was computed, to indicate how much of the variance among fraction means can be assigned to the position in the incubator with $\eta^2$~0.039 small, $\eta^2$~0.11 medium and $\eta^2$~0.2 large effect size.
Figure 12:
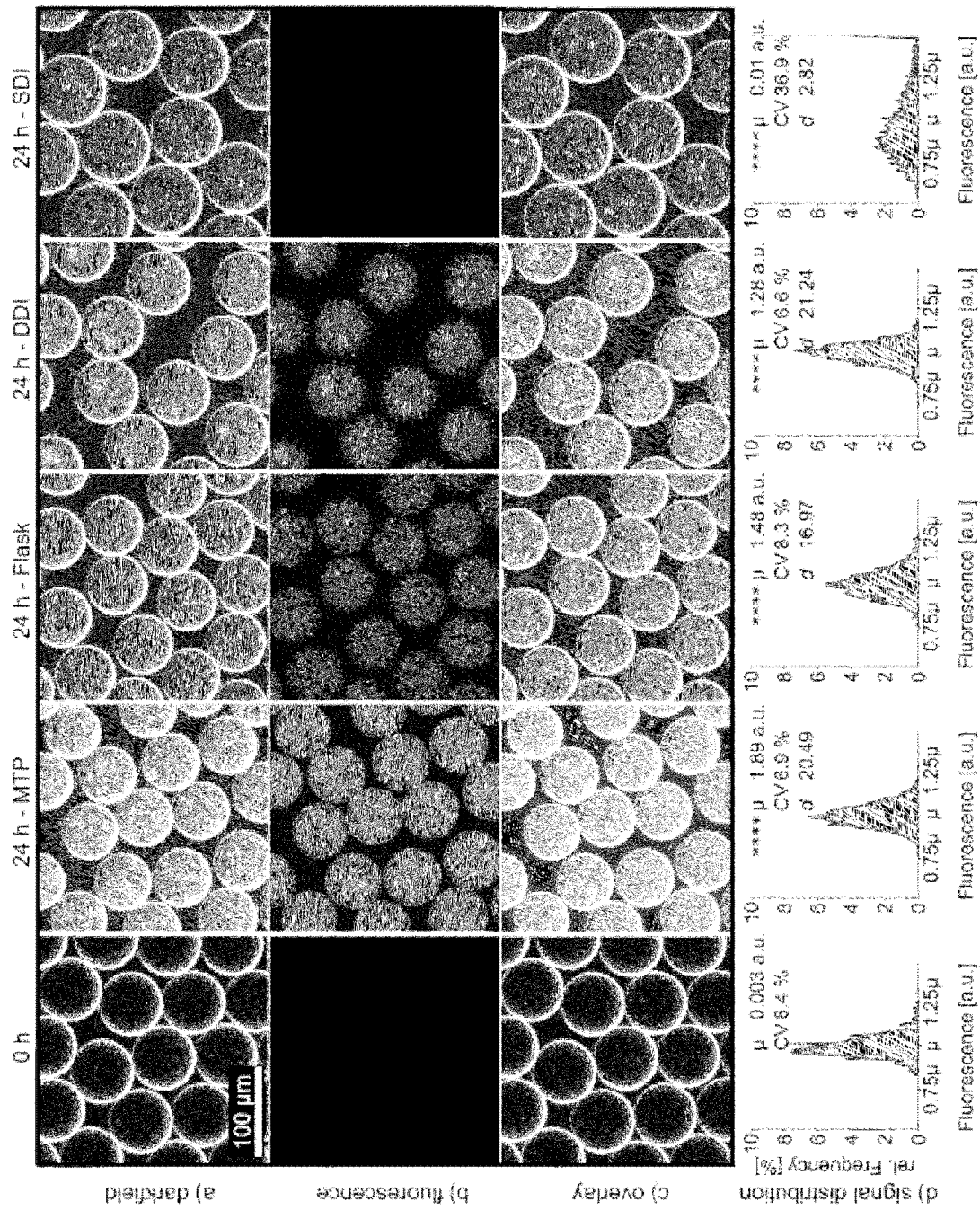
FIG. 12: depicts mCherry fluorescence intensity of droplets either re-injected after 24 h of DDI and SDI or generated from 24 h MTP and shaking flask cultures. Images were recorded in darkfield (a) and fluorescence mode (b) at 10× magnification. The fluorescence images were enhanced in brightness for the overlay (c). Frequency distributions of fluorescence intensity of at least 600 droplets per cultivation method (d). Means of fluorescent intensity were compared with Welch corrected ANOVA and Dunnett's test (both $\alpha=0.05$) in combination with a heteroscedastic consistent covariance estimation, **** significant with p<0.0001. As a measure of effect size Cohen's d is computed, using 0 h control as reference. Remarkably, the effect size of SDI is one magnitude smaller than the effects of MTP, shaking flask or DDI.

However, in the sense of this invention, the term "circuit" can also mean that it is preferable that the carrier fluid is led, for example, from a large reservoir, which is arranged preferably above the droplet incubator, into the droplet incubator. This preferred embodiment is represented in FIG. 6. Although the flow-through conduit in this preferred design of embodiments of the invention do not form a closed circuit for the carrier fluid, the average person skilled in the art nonetheless knows how the carrier fluid, after it has passed once through the droplet incubator, can be returned to the large reservoir to be enriched again with useful gas. It can be preferable that the carrier fluid flows on its own into the droplet incubator, due to its positional energy resulting from the arrangement of the reservoir above the droplet incubator. Or, it can also be preferable that, in order to convey the carrier fluid, one of the above-mentioned pumps is provided in the connection between the droplet incubator and the reservoir, and it propels the carrier fluid, instead of the positional energy or in addition thereto. In this embodiment of the invention, the flow through the system is not implemented by a closed circuit consisting of flow-through conduit; instead the positional energy of the carrier fluid is used at least partially for propelling the carrier fluid.

It was entirely surprising that, in this preferred embodiment of the invention as well, a continuous flow through the system according to embodiments of the invention can be achieved. This is particularly advantageous if a large amount of carrier fluid is available and space for a large reservoir container is present. Advantageously, after the carrier fluid has passed through the droplet incubator and has released the useful gas to the microfluidic droplets, it is collected so that it can be filled again into the reservoir or used for other purposes. Thus, for this embodiment as well a resource-saving use of the carrier fluid is surprisingly made possible.

Preferably, the droplet incubator has an outlet formed by flow-through conduit, wherein the flow-through conduit connect the droplet incubator and the conveyor. It is advantageous that the flow-through conduit that connect the droplet incubator and the conveyor to one another are filled completely with the carrier fluid and the gases or gas mixtures contained therein. This is achieved advantageously by the fact that the flow-through conduit form a circuit in which the carrier fluid is moved continuously. As represented in FIGS. 1 to 6, the circuit is formed preferably by flow-through conduit which connect the individual components of the system according to embodiments of the invention to one another, particularly the droplet incubator, the gas exchanger and the conveyor. In the circuit, it is preferable that the carrier fluid enriched with a gas or gas mixture is moved. It is preferable both that the flow-through conduit form a closed circuit, as represented in FIGS. 1 to 5, and also that the circuit of the flow-through conduit is not closed. The propelling of the carrier fluid preferably occurs by means of the conveyor, as a result of which movement of the carrier fluid, oriented preferably in the same direction, is produced in the circuit. In the preferred embodiment of the invention represented in FIG. 6, it can also be preferable for the propulsion of the carrier fluid to occur without conveyor, but instead due to a difference in height and positional energy between the large reservoir and the droplet incubator.

Via an additional outlet of the droplet incubator, an integration of the system according to embodiments of the invention in complex test assemblies is possible. It is preferable that this outlet is situated in the lower area of the droplet incubator and that the flow-through conduit, which is situated at this outlet of the droplet incubator, has a valve. The lower area of the droplet incubator is formed here, for example, by a bottom surface of the container forming the droplet incubator or by its side faces. Moreover, it is preferable that the droplet incubator has an additional outlet in the lower area, which is connected by a flow-through conduit to the conveyor. By means of this flow-through conduit, the circuit between conveyor, droplet incubator and gas exchanger is preferably closed, wherein, by means of the flow-through conduit between droplet incubator and conveyor, the carrier fluid, which has released the useful gas present in the droplet incubator and which has received the waste gas converted by the cell cultures, flows back to the conveyor.

It was entirely surprising that, by means of the arrangement of the flow-through conduit according to embodiments of the invention and the connection of the system components to the flow-through conduit, a closed circuit including a gas source can be provided, which allows a continuous flow of the carrier fluid enriched with the gases or gas mixtures through the system according to embodiments of the invention. Advantageously, the design of the closed circuit allows the surprisingly uniform flow around the cell cultures within the microfluidic droplets, thus ensuring the surprisingly uniform supply of useful gas to the cell suspension and/or dissolved reagents.

It is preferable that the droplet incubator is produced from materials selected from polypropylene, PTFE, glass, metals and/or materials that can be processed in 3D printing and/or by stereolithography methods, and/or from any combinations of these substances.

The conveyor leads the carrier fluid, in particular continuously, through the closed circuit for the carrier fluid, which is formed by flow-through conduit and droplet incubator and gas exchanger, or, when the positional energy of the carrier fluid is exploited, from the reservoir into the droplet incubator. Here, the carrier fluid travels a distance s as it passes through the gas exchanger. It is preferable that, on the conveyor, different flow rates of the carrier fluid can be set. Depending on the set flow rate, the time period t which the carrier fluid needs to pass through the gas exchanger varies. It is preferable that the residence time t can be approximated by calculating the quotient t=volume/volume flow. During the time period t, a gas exchange preferably occurs in the gas exchanger. This gas exchange occurs preferably at the phase boundary between the carrier fluid and the gases or gas mixtures located in the upper area of the gas exchanger. However, it can also be preferable for the gas exchange to be implemented by introducing the gases or gas mixtures into the carrier fluid through the flow-through conduit coming from the gas source.

By the gas exchange that occurs in the gas exchanger, the carrier fluid is enriched with the gases or gas mixtures present in the upper area of the gas exchanger. Advantageously, the gases or gas mixtures introduced in the gas exchanger into the carrier fluid are the useful gas that is converted into a waste gas by the cell cultures present in the microfluidic droplets in the droplet incubator. Also, advantageously, the gases or gas mixtures introduced into the carrier fluid can displace gases that are not desired for the respective application, so that cell cultures or reagents present in the droplets are not exposed to the undesired influence of these gases.

By enriching the carrier fluid with the useful gas and by the cyclic and continuous transport of the carrier fluid which comprises the useful gas into the droplet incubator, a uniform flow of the carrier fluid around the microfluidic droplets is achieved in the droplet incubator, as a result of which a surprisingly consistent satisfactory supply of the useful gas to the cell suspensions or to the dissolved reagents within the droplets is achieved. It was entirely surprising that, in this manner, the providing of a targeted introduction of the useful gas into the microfluidic droplets, or a continuous useful gas supply which can be maintained over a long time period, is possible. It was entirely surprising that the gas flow for the gas exchange occurring in the gas exchanger does not have to be interrupted but can instead be carried out continuously.

In another preferred embodiment, the invention relates to a system wherein the gas exchanger is formed at least partially by the flow-through conduit, and the flow-through conduit consist of gas-permeable materials. It is preferable for the flow-through conduit that form the gas exchanger to be present wound on a coil and for an exchange to take place between the gases or gas mixtures located outside of the gas-permeable flow-through conduit, and the gases or gas mixtures that are present dissolved in the carrier fluid. Advantageously, the gases or gas mixtures located outside of the gas-permeable flow-through conduit are the useful gas, which is converted by the cell suspensions or the dissolved reagents in the microfluidic droplets into a waste gas. It is preferable that the gas-permeable flow-through conduit are produced from materials selected from: polytetrafluoroethylene (PTFE), silicone, FEP, perfluoroalkoxy polymers (PFA) and/or other gas-permeable polymers. Polytetrafluoroethylene is an unbranched, linearly structured, partially crystalline polymer made of fluorine and/or carbon, which belongs to the class of the polyhalogen olefins. Silicone refers to a group of synthetic polymers in which silicon atoms are linked by oxygen atoms. FEP is a plastic from the group of the fluorocarbons. Perfluoroalkoxy polymers are completely fluorinated plastics, copolymers made of tetrafluoroethylene and perfluoroalkoxyvinyl ethers such as perfluorovinylpropyl ether, for example.

The average person skilled in the art knows which other materials can be used as flow-through conduit. Preferably materials that are inert are used, that is to say materials that do not react with the carrier fluid or the useful gas. Tests have shown that PTFE and/or silicone, in particular, have a surprisingly good gas permeability. In addition, for example, flow-through conduit made of hydrophobic material can be used, if the gas-permeable flow-through conduit are also to be used for the transport of the microfluidic droplets.

In another preferred embodiment, the invention relates to a system in which the gas exchanger is arranged in a gas-tight enclosure, wherein the enclosed volume in the gas-tight enclosure forms the reservoir of the gas exchanger. It can also be preferable if the system according to embodiments of the invention is completely surrounded by a gas-tight enclosure. In the sense of embodiments of the invention, the term "enclosure" preferably refers to a container which is closed in a gas-tight manner with respect to the ambient atmosphere. In the context of this invention, the term "housing" is used synonymously for the term "enclosure." Advantageously, the composition of the gaseous content of the gas-tight container of the housing can be monitored and regulated. It is particularly preferable for the gas exchanger to be in that case arranged in a gas-tight enclosure, if the gas exchanger is formed by the gas-permeable flow-through conduit.

Advantageously, the enclosure can then be filled with a gas which is preferably different from oxygen or an air mixture that contains oxygen. Advantageously, the gas can also be air that is enriched with oxygen, or exclusively oxygen. This gas is then enriched by means of the gas exchange in the carrier fluid, which is present in the flow-through conduit, said exchange occurring through the gas-permeable flow-through conduit, and said gas is led as useful gas into the droplet incubator. The use of gases or gas mixtures that contain no oxygen is particularly advantageous if, in the microfluidic droplets in the droplet incubators, such reagents, suspensions or cells are incubated and/or multiplied, that do not metabolize oxygen, or, on the other hand, for which the presence of oxygen does not represent an optimal condition. The average person skilled in the art knows how to procure and set up a gas-tight enclosure, so that it is closed in a gas-tight manner with respect to the ambient atmosphere.

Moreover, it is preferable that the housing can be used not only for the purpose of providing a useful gas that is different from air, but also for the purpose of exposing the housing to a high pressure or low pressure, and thus, on the basis of any pressure differences between the atmosphere within the housing and the carrier fluid within the closed circuit of the system according to embodiments of the invention, promoting or slowing the uptake and release of the useful gas by the carrier fluid.

Moreover it is preferable that the reservoir is filled with gas mixtures different from air, as gas source. The reservoir represents a container which forms a component of the gas exchanger. In this container, the carrier fluid is located in a lower area, and gas or gas mixture is located in an upper area.

According to an embodiment of the system according to embodiments of the invention, the reservoir is connected in a gas-open manner to the ambient atmosphere. The term "gas-open," in the sense of this invention, means that a flow-through conduit or a container in which a gas is moving has a construction such that the gas can flow through without impediment and that the flow-through conduit comprises no gas barrier, in particular. According to this embodiment, the gas source is formed by the ambient atmosphere, which usually comprises an air mixture in the usual composition. As a result of the gas-open connection of the reservoir of the gas exchanger with the ambient atmosphere, air, as a component of the gas source, reaches the carrier fluid present in the reservoir. As a result of the operation of the conveyor, it is pumped by a flow-through conduit into the droplet incubator, wherein it is received through an opening in the cone tip of the droplet incubator, which tapers to a point. In this embodiment of the invention it is preferable that the useful gas, which is converted by the cell cultures in the microfluidic droplets, is air. It was entirely surprising that the flow-through conduit represents a diffusion barrier whose properties depend on the material of which the flow-through conduit is made and on its wall thickness.

However, it is also preferable that the reservoir is filled with a gas mixture, as gas source, which is different from air. In this case, the gas mixture, as useful gas, which is different from air, reaches the microfluidic droplets in the droplet incubator where it is converted in the microfluidic droplets by the cell cultures, cell suspensions or dissolved reagents into a waste gas. In the sense of embodiments of the invention, it is also preferable that no waste gas forms in some applications, particularly in the chemical or physical field. Due to the flexible design of the reservoir and the possible use of different gases as consumption gas in the system according to embodiments of the invention, a broad application of the system is surprisingly made possible, for a large number of different microorganisms and/or cell cultures.

In a further preferred embodiment, the system comprises means for the acquisition and/or regulation of the concentration of dissolved gases or gas mixtures, in particular oxygen. The average person skilled in the art knows which means can be used for the determination of a concentration of dissolved gases or gas mixtures, for example, oxygen, in the system according to embodiments of the invention. These means comprise all known types of gas sensors whose mode of operation is based on physical, chemical, resistive, capacitive, potentiometric, amperometric, thermal, thermophysical, thermochemical, optical, gravimetric and/or biochemical principles or any combination thereof.

In a further preferred embodiment, embodiments of the invention relate to a system in which the conveyor comprises means for generating a cyclic and continuous flow of the closed circuit, consisting of droplet incubator, gas exchanger and flow-through conduit. The means for generating a cyclic and continuous flow-through can be formed by a peristaltic pump, for example. In the sense of embodiments of the invention, a peristaltic pump denotes a pump which is based on the principle of displacement and in which the carrier fluid to be conveyed is pressed by an external mechanical deformation of the flow-through conduit through said flow-through conduit, wherein, in the area of the peristaltic pump, the flow-through conduit preferably are made from different materials than the flow-through conduit which connect, for example, the gas exchanger and the droplet incubator or the conveyor and the gas exchanger to one another. Preferably, in the area of the peristaltic pump, PFTE should be used as material for the flow-through conduit, since it cannot be squeezed.

Advantageously peristaltic pumps emulate the principle of conveyance of fluids in cylindrical hollow organs, as it is known from biology. The cylindrical hollow organ constricts at a site, and this constriction moves along the length of the hollow organ. It was entirely surprising that the peristaltic pumps are suitable particularly for conveying fluids that are loaded with particles or have a high viscosity. It is preferable that this type of pump dispenses with valves, seals and rotating parts within the fluid-conducting elements. Moreover, it was entirely surprising that as a result abrasion and wear at edges or irregular courses of the pump surface due to collision with hard particles from a suspension are avoided.

It is preferable that the conveyor, as a component of the system according to embodiments of the invention, comprises two inlets for flow-through conduit. Preferably, a flow-through conduit leads away from the conveyor into the reservoir of the gas exchanger and ends in the upper gas-filled area of the reservoir. The conveyor is connected by means of the flow-through conduit via an additional outlet to the outlet of the droplet incubator.

Moreover, it is preferable for the flow-through conduit coming from the droplet incubator to be clamped into the conveyor. Advantageously, the conveyor actuates the carrier fluid by compressing the flow-through conduit through the closed circuit of the system according to embodiments of the invention. It is preferable that the outer mechanical deformations of the flow-through conduit, which are referred to as compression components of the conveyor in the sense of this invention, are present designed as rollers that are attached to a rotating wheel. Due to the rotation of the wheel, the rollers are positioned on the flow-through conduit and rolled with exertion of pressure over the flow-through conduit. Advantageously, as a result of the application of this outer force onto the flow-through conduit, the carrier fluid is pressed in a surprisingly reliable and stable manner in a constant direction.

When the system according to embodiments of the invention is used for incubating microfluidic droplets, it is preferable for the carrier fluid to be moved by the conveyor in the direction of the gas exchanger. It is possible advantageously to set the rotational speed of the wheel which guides the rollers on the conveyor. Taking into consideration the rotational speed of the pump wheel and the inner diameter of the flow-through conduit to be used, the flow rate of the carrier fluid can be set. For example, the flow rate of the carrier fluid can preferably be in a range from 0.6 to 60,000 µL/min, particularly preferably 1 to 20,000 µL/min, most preferably between 10 and 3000 µL/min and most preferably of all from 50 to 700 µL/min per minute.

The average person skilled in the art knows that the speed of the wheel depends on the diameter of the flow-through conduit used, the constitution and the flow properties of the carrier fluid, and the total volume of the system according to embodiments of the invention, and he is able to adjust the rotational speed of the wheel to these conditions. In the sense of this invention, it is preferable to convert the rotational speed of the wheel, which is indicated in the units "rounds per minute," to a flow rate of the carrier fluid, which is indicated in the unit "microliter per minute" (µL/min). It was entirely surprising that, using the wheel of the conveyor, the flow rate of the carrier fluid through the closed circuit of the system according to embodiments of the invention can be set in particularly small increments and as a result with particular precision.

However, in the closed circuit consisting of flow-through conduit of the system according to embodiments of the invention, it can also be preferable to provide means for the determination of the flow rate of the carrier fluid. This is particularly advantageous if the precise determination of the flow rate at a certain site of the closed circuit is important. Deviations from the flow rate that is set on the wheel of the conveyor can result, for example, from the fact that the flow-through conduit do not have a constant diameter at every site of the closed circuit consisting of flow-through conduit of the system according to embodiments of the invention. The average person skilled in the art knows that narrowing of a flow-through conduit can lead to an increased flow rate in this area. The average person skilled in the art also knows that a broadening of a flow-through conduit leads to a reduction of the flow rate.

It is preferable that the flow rate in the closed circuit consisting of flow-through conduit correlates with a pump rate which indicates how frequently per day a complete volume turnover of the carrier fluid is carried out, for example, in the droplet incubator. It was entirely surprising that it is possible to reach a number of up to 10,000 complete volume turnover processes per day. In the same way, it was entirely surprising that the flow rate in the closed circuit of the system according to embodiments of the invention can be reduced sufficiently strongly so that pump rates of 0.1 volume turnover processes per day can be reached. It is preferable that the pump rates achieved in the closed circuit of the system according to embodiments of the invention fall between these two extreme values.

It was entirely surprising that, by means of the regulation of the flow rate through the conveyor, the amount of useful gas transferred from the carrier fluid to the microfluidic droplets can be varied and/or set. It has been shown that, for example, a high flow rate v of the carrier fluid correlates with a larger amount of the transferred gas or gas mixtures, while low flow rates v of the carrier fluid are associated with smaller amounts of the gas or gas mixtures.

In an additional preferred embodiment, the invention relates to a system in which a simultaneous incubation of preferably 10,000 to 10 billion, particularly preferably 500,000 to 500 million, most preferably 2 million to 20 million, and most preferably of all 3 million to 7 million microfluidic droplets is ensured. It was entirely surprising that parallel culturing of such a large number of microfluidic droplets comprising a cell suspension and/or other dissolved reagents is possible. So far, the professional community has not seen a need to provide homogeneous and reproducible conditions with regard to the gas supply for the incubation of such large numbers of microfluidic droplets. The result of this was a deficiency of useful gas within the microfluidic droplets, which affected the cell suspensions and the dissolved reagents within the microfluidic droplets.

Moreover, it is preferable that the total gas volume of the incubated microfluidic droplets falls in a range from preferably 1 µL to 1 L, particularly preferably in a range from 100 µL to 100 mL, most preferably in a range from 1 mL to 10 mL. Here, the range from 10 µL to 1 L is particularly advantageous if particularly small or large systems are to be provided, for example, in the case where the spatial circumstances of the setup location require this.

Advantageously, the system according to embodiments of the invention allows a continuous flow of a carrier fluid, in which the useful gas is present dissolved, around the microfluidic droplets, wherein the carrier fluid flows preferably in a circuit. The continuous and cyclic flow of the carrier fluid through the droplet incubator then leads to new, unconsumed useful gas continuously reaching the droplet incubator, which allows a homogeneous distribution of the gas within the droplet incubator. A homogeneous supply of the microfluidic droplets with unused useful gas is thus surprisingly ensured by the system according to embodiments of the invention as is the advantageous cooperation of the system components according to embodiments of the invention.

In another aspect, embodiments of the invention relate to a method for providing homogeneous incubation conditions in a droplet incubator by targeted introduction of gases or gas mixtures into a carrier fluid, which comprises the following steps:

a) generation of a continuous flow of the carrier fluid through a droplet incubator b) first exchange of at least a portion of the gases or gas mixtures dissolved in the carrier fluid during a residence time of the carrier fluid in a gas exchanger c) second exchange of at least a portion of the gases or gas mixtures dissolved in the carrier fluid, during the flow of the carrier fluid through the droplet incubator.

It was entirely surprising that a method for providing homogeneous incubation conditions in a droplet incubator can be provided, in which, due to a targeted introduction of gases or gas mixtures into a carrier fluid, an incubation of cell cultures, cell suspensions or dissolved reagents in the droplet incubator can be implemented with the quality observed and with such a large number of microfluidic droplets incubated in parallel. So far, the professional community had assumed that, in the field of droplet-based microfluidics, supplying the microfluidic droplets with the useful gas, in particular oxygen, is sufficient when using the method known from the prior art. Comparison tests between the method according to embodiments of the invention and microfluidics methods from the prior art have shown that the gas supply of the microfluidic droplets can be improved decisively by using the method according to embodiments of the invention. This is achieved advantageously in that a continual new enrichment of the carrier fluid with the useful gas occurs, which results in preferably fresh useful gas which is dissolved in the carrier fluid being supplied to the microfluidic droplets in the droplet incubator.

By the generation of a cyclic or continuous flow of the carrier fluid through a closed circuit formed by flow-through conduit, the droplet incubator and a gas exchanger, the method according to embodiments of the invention advantageously allows a homogeneous distribution of the useful gas in the droplet incubator, so that higher cell densities can be achieved surprisingly in comparison to the conventional microfluidic culturing methods known in the prior art.

Moreover, the generation of a cyclic or continuous flow of the carrier fluid through a closed circuit allows preferably a first gas exchange in the gas exchanger. Analogously to the pulmonary circulation of human blood, the carrier fluid takes up a useful gas in the gas exchanger, which can be formed by a gas or a gas mixture and releases the waste gas which has been converted in the microfluidic droplets, said waste gas being transported by the carrier fluid from the droplet incubator through flow-through conduit into the gas exchanger. It is preferable that the carrier fluid with the dissolved waste gases, which can also consist of gases or gas mixtures, is propelled by the conveyor.

Advantageously, in the gas exchanger, the useful gases are taken up by the carrier fluid, said useful gases having been converted or metabolized in the microfluidic droplets in the droplet incubator by the processes that occur there. Depending on the type of cell suspension or the dissolved and/or suspended reagents, cell-free systems, microorganisms, eukaryotic cells and/or chemical or materials science materials, the gases or gas mixtures are preferably selected from the group comprising: nitrogen, nitrogen mixtures, rare gases, air, air mixtures, oxygen, hydrogen, carbon dioxide, gas mixtures and/or any conceivable combination of the mentioned gases.

It is preferable that the exchange of the gases or gas mixtures in the gas exchanger occurs at least partially. However, it can also be preferable that a complete gas exchange occurs. Moreover, it is preferable that the exchange of the gases in the gas exchanger occurs during a residence time or a residence duration t of the carrier fluid in the gas exchanger. Depending on the set flow rate v, the time t varies. It is preferable that the residence time t can be approximated by calculating the quotient t=volume/volume flow.

The method according to embodiments of the invention moreover preferably comprises a second exchange between a part of the gases or gas mixtures dissolved in the carrier fluid, during the flow of the carrier fluid through the droplet incubator. In the context of this second gas exchange, the carrier fluid in the droplet incubator releases the entrained useful gas to the microfluidic droplets located in the droplet incubator. The droplets take up the useful gas, which is converted by the cell cultures and microorganisms within the microfluidic droplets into waste gas. It was entirely surprising to the average person skilled in the art that, due to the transport processes within the microfluidic droplets, the waste gas comes out of the microfluidic droplets and is entrained by the carrier fluid due to the high affinity of the carrier fluid for gas atoms or gas molecules.

It is preferable that the second exchange within the droplet incubator represents a reversal process relative to the first gas exchange within the gas exchanger. The reversal consists in that, in the context of the first exchange, the carrier fluid takes up the useful gas and releases used waste gas, while, in the context of the second exchange, the carrier fluid releases the useful gas within the droplet incubator to the microfluidic droplets, and it takes up the waste gas converted in the microfluidic droplets and advantageously discharges it from the droplet incubator.

In a further preferred embodiment, the invention relates to a method for providing homogeneous incubation conditions in a droplet incubator, wherein the method comprises providing of a carrier fluid with a plurality of microfluidic droplets in the droplet incubator. It is preferable that, for carrying out the method according to embodiments of the invention, a plurality of microfluidic droplets are provided in the droplet incubator using means and methods that in themselves are known. The number of the microfluidic droplets here is preferably in a range from preferably 10,000 to 10 billion, particularly preferably 500,000 to 500 million, most preferably 2 million to 20 million and most preferably of all 3 million to 7 million microfluidic droplets. It was entirely surprising that the method according to embodiments of the invention can be carried out with such a large number of microfluidic droplets to be cultured in parallel. To that extent, the method according to embodiments of the invention represents a turning away from what has been technically conventional so far, since the professional community assumed so far that parallel culturing of a large number of microfluidic droplets has been impossible due to the lack of a method for ensuring reproducible growth conditions and a regular supply with useful gases.

In a preferred embodiment the system is characterized in that the system comprises means to determine the oxygen concentration within the microfluidic droplets and the system is configured such that the flow rate of the carrier fluid is adjusted according to the measured oxygen concentration.

Herein the term oxygen concentration preferably refers to the dissolved oxygen concentration within the aqueous solution that constitutes the droplet. A person skilled in the art knows which devices and/or means are necessary to measure the oxygen concentration within droplets. Dissolved oxygen concentration (DO) inside droplets can be for instance measured by means of nano probe-based, oxygen-sensitive NIR-luminescence measurements, which enable a biocompatible, non-invasive measurement. To this end the nanoprobes are dispersed in the aqueous phase of the droplets. A preferred nanoprobe is a dye that is excitable by orange-red light and shows an oxygen-dependent luminescence in the near-infrared (NIR) regime as for instance REDFLASH dyes from pyroscience. The NIR-luminescence may be measured through the transparent housing of the droplet incubator by a fiber-optic oxygen meter that determines the dissolved oxygen concentration based upon the measured NIR-luminescence. Within the scope of the preferred embodiment it may however also be preferred to use other oxygen-sensitive nanoprobes or equivalent probes that may serve as sensors for the dissolved oxygen concentration in the droplets.

It is preferred that the oxygen concentration is measured for preferably more than 5%, more preferably more than 20% and most preferably more than 50% of the population of the droplets that are incubated. It may however also be desired to measure the oxygen concentration within a smaller number of microfluidic droplets. It is however preferred that the number of microfluidic droplets for which the oxygen concentrations are measured is sufficiently large to arrive at a representative estimation of the oxygen concentration within the population of microfluidic droplets. It is further preferred that based upon the measurement an average oxygen concentration is determined. It is further preferred that the system comprises means to regulate the flow rate of the carrier fluid, which can be for instance a pump that is electronically controllable. It is further preferred that the flow rate of the carrier fluid is regulated based upon the measurement oxygen concentration. To this end the system may comprise for instance additionally a data processing unit that is connected to said electronically controllable pump. The preferred system therefore advantageously comprises means for a feedback control for the flow rate of the carrier fluid that depends on the oxygen concentration inside the microfluidic droplets. As described above the transfer of oxygen into the droplets is increased due to the dynamic incubation that is in particular a configuration in which the carrier fluid is continuously or sporadically flowing. With the flow of the carrier fluid the oxygen transfer towards the droplets can be advantageously controlled. Therefore it is preferred that the flow rate of the carrier fluid is increased or decreased in case the measured oxygen concentration rate falls below or above a predefined threshold. For instance it may be preferred that the dissolved oxygen concentration is kept in between a predefined range for instance in between 4 mg/ml to 8 mg/ml. The preferred range will depend on the application. It may also be preferred that the range of the oxygen concentration is set such that the oxygen concentration is substantially constant. Herein a substantially constant oxygen concentration preferably refers to an oxygen concentration that deviates less than 10% more preferably less than 5% from the desired oxygen concentration. To arrive at an oxygen concentration in between a preset range the flow rate of the carrier fluid is increased once the oxygen concentration falls under the lower limit of the range, while it is decreased once the oxygen concentration exceeds the upper limit of the given range. It was surprising that by such a feedback loop particular stable incubation conditions could be achieved. Such a feedback loop is particularly advantageous for cell cultivation applications, in which it is desired that the cells are kept at a physiological oxygen level. Moreover the feedback loop is flexible, since it can adapt to a range of desired oxygen concentration for different applications, which may depend on the incubated content of the droplet e.g. the type of cells, microorganisms, enzymes etc. Furthermore the preferred embodiment advantageously allows for a dynamic regulation of the oxygen concentration within the population of droplets. For instance it may be desired to increase the oxygen concentration for a given time point and/or time range. Surprisingly this can be efficiently achieved by a controlled increase of the flow rate of the carrier fluid for said time point and/or time range. It was particularly surprising that by these means the oxygen concentration could be regulated homogeneously within the population of droplets within a high dynamic range. Moreover it may also be preferred that the system includes a feedback loop that is not based upon the oxygen concentration within the microfluidic droplets, but based upon the concentration of a different gas preferably selected from carbon dioxide, hydrogen, methane, hydrogen sulfide, nitrogen and/or any mixture thereof.

FIG. 1 shows a preferred embodiment of the system consisting of droplet incubator (10) and conveyor (22) as well as of a gas exchanger (26), wherein the gas exchanger (26) is formed by the flow-through conduit (20). Represented is a closed circuit for the flow of a carrier fluid (12), which is formed by flow-through conduit (20) and which comprises a conveyor (22), for example, a peristaltic pump, as well as a droplet incubator (10). The droplet incubator (10) is formed by a cylindrical lower part (10 a) and a conical upper part (10 b). FIG. 1 represents the preferred embodiment of the system according to the invention, in which the upper part (10 b) of the droplet incubator (10) is situated above the lower part (10 a) of the droplet incubator (10), that is to say it is at a greater distance from the substrate than the lower part (10 a) of the droplet incubator (10). The upper part (10 b) of the droplet incubator (10) narrows upward and it is closed off by a fitting (16) which has a passage for the flow-through conduit (20).

In this narrowing section of the upper part (10 b) of the droplet incubator (10), in the represented preferred embodiment of the system, the microfluidic droplets (not shown) collect, forming an aqueous phase separate from the carrier fluid (12) and an apparently cohesive droplet volume. The phase boundary forming between the generally oily carrier fluid (12) and the aqueous phase which comprises the microfluidic droplets is referred to as overall phase boundary in the context of this invention.

Through the fitting (16a), which is inserted in the upper part (10 b) of the droplet incubator (10), the carrier fluid (12) reaches the droplet incubator (10) by means of the flow-through conduit (20). The flow direction (14) of the carrier fluid (12) through the components of the system according to embodiments of the invention is provided with reference numeral 14 in FIGS. 1 to 6.

According to the representation in FIG. 1, the bottom of the lower part (10 a) of the droplet incubator (10) is provided with two openings, which again can be formed by fittings (16b and 16c) and which connect the droplet incubator (10) to flow-through conduit (20). One of these flow-through conduit (20) leads to an additional complex test assembly in which the discharged material which has been incubated beforehand in the microfluidic droplets can be examined. The discharge occurs by means of a valve (18 b). Through a second outlet, which is formed by an additional fitting (16 c), the carrier fluid (12) can reach an additional flow-through conduit (20) which leads to a conveyor (22).

FIG. 1 shows that the flow-through conduit (20) together with the system components consisting of conveyor (22) and droplet incubator (10) form a closed circuit for the carrier fluid (12), wherein the conveyor (22) allows a continuous flow of the carrier fluid (12) through the droplet incubator (10). After the passage of the carrier fluid (12) through the conveyor (22), the carrier fluid (12) is moved through additional flow-through conduit (20) in the direction of the droplet incubator (10), wherein an additional valve (18a) is provided in the flow-through conduit (20), which is located between the droplet incubator (10) and the conveyor (22).

In the embodiment of the system according to the invention shown in FIG. 1, the gas exchange, by means of which the carrier fluid (12) is enriched with "fresh" useful gas, occurs through the flow-through conduit (20) which have a gas-permeable design. Accordingly, gas atoms or gas molecules of the gas or gas mixture surrounding the system can penetrate through the material of the flow-through conduit (20) and in this way reach the inner space of the flow-through conduit (20) which is filled with the carrier fluid (12). It is preferable that these gases or gas mixtures are the useful gas (28) provided for the processes within the microfluidic droplets. Due to the affinity of the carrier fluid (12) for the offered molecules or atoms of the gas or gas mixture, the gas components are dissolved or enriched in the carrier fluid (12) and transported by said carrier fluid (12) through the system according to embodiments of the invention.

At the tip of the upper part (10b) of the droplet incubator (10) are the microfluidic droplets in the aqueous phase, comprising cell suspensions and/or reagents (not shown). Here, an exchange of the gases or gas mixtures dissolved in the carrier fluid (12) occurs, wherein the "useful gas" (28) taken up in the flow-through conduit (20) is released to the microfluidic droplets. If a waste gas has formed due to the processes within the microfluidic droplets, this waste gas is taken up by the carrier fluid (12) and transported away due to the continuous flow of the carrier fluid (12) through the droplet incubator (10). Due to the continuous addition of "fresh" carrier fluid (12) enriched with a useful gas (28), a regular and homogeneous supply of the useful gas (28) to all the microfluidic droplets is achieved.

Figure 2:
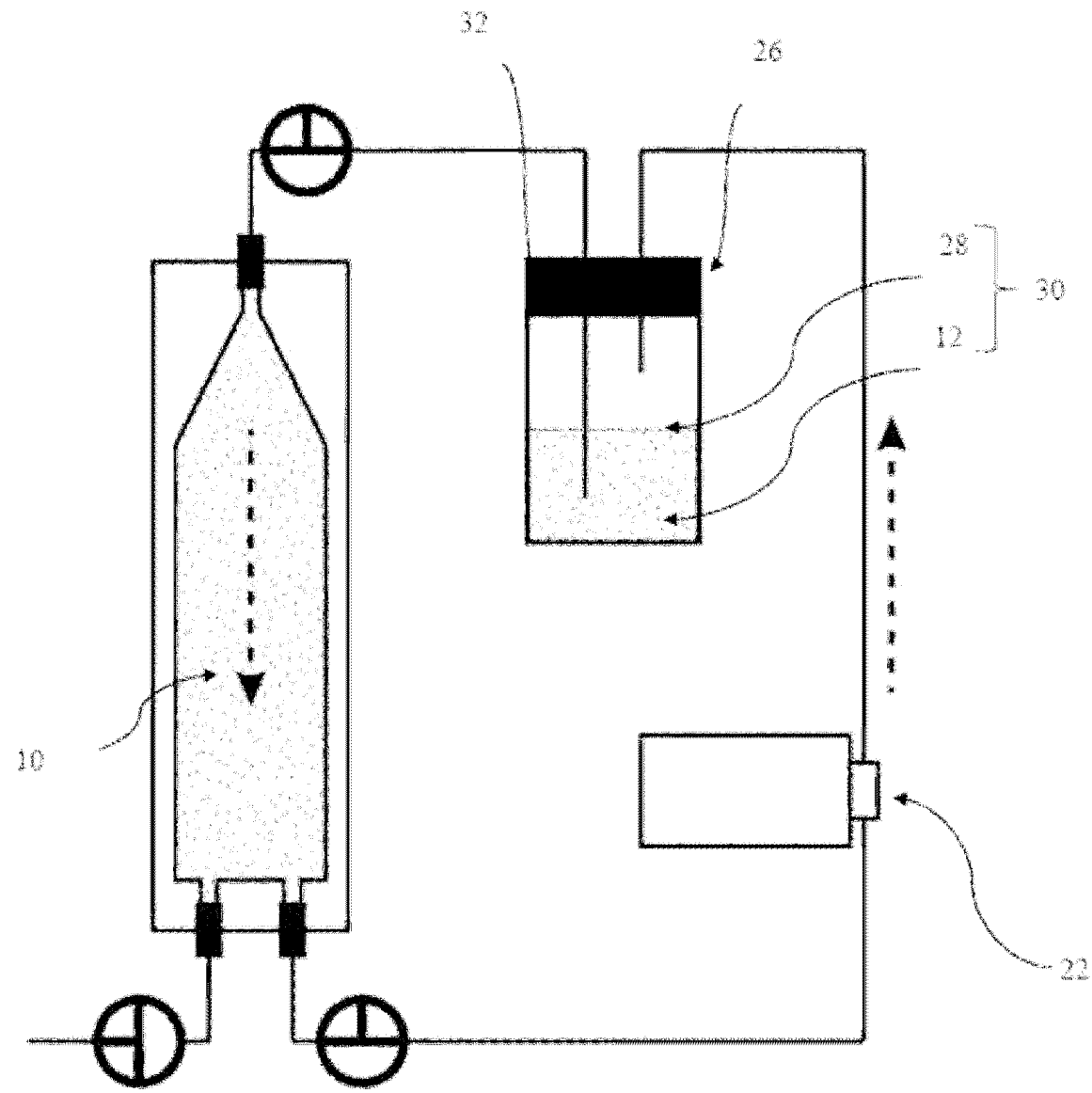
FIG. 2: A representation of a preferred embodiment of a system according to the invention, which, in addition to the components represented in FIG. 1, comprises a gas exchanger (26) with a reservoir (30) in which the carrier fluid (12) is located in a lower area and the useful gas (28) is located in an upper area, wherein the reservoir (30) is closed by a cover (32) with passages for the flow-through conduit (20).

According to the embodiment of the invention shown in FIG. 2, a gas exchanger (26) is provided between the conveyor (22) and the upper part (10 b) of the droplet incubator (10). The gas exchanger (26) is connected to the conveyor (22) via flow-through conduit (20), wherein the flow-through conduit (20), through the cover (32), arrives in the reservoir (30) of the gas exchanger (26) and ends in the upper area of the reservoir (30) which is filled with useful gas (28). An additional flow-through conduit (20) connects the gas exchanger (26) to the upper part (10 b) of the droplet incubator (10), wherein the flow-through conduit (20), which arrives through the cover (32) in the gas exchanger (26), ends in the carrier fluid (12) which is located in the lower area of the gas exchanger (26). Through the last-mentioned flow-through conduit (20), the carrier fluid (12) arrives from the gas exchanger (26) in the droplet incubator (10), after a gas exchange has taken place within the carrier fluid (12) upon the passage of the carrier fluid (12) through the gas exchanger (26).

The upper area of the gas exchanger (26) is filled with a gas or gas mixture, preferably the useful gas (28), which is needed for the processes that occur in the microfluidic droplet. Due to the presence of the useful gas (28) in the upper area of the gas exchanger (26) and due to the affinity of the carrier fluid (12) for the gas or gas mixture, an enrichment of the useful gas (28) within the carrier fluid (12) occurs, that is to say now components of the gas or gas mixture are dissolved in the carrier fluid (12) and with this carrier fluid (12) they arrive in the droplet incubator (10) through the flow-through conduit (20).

Figure 3:
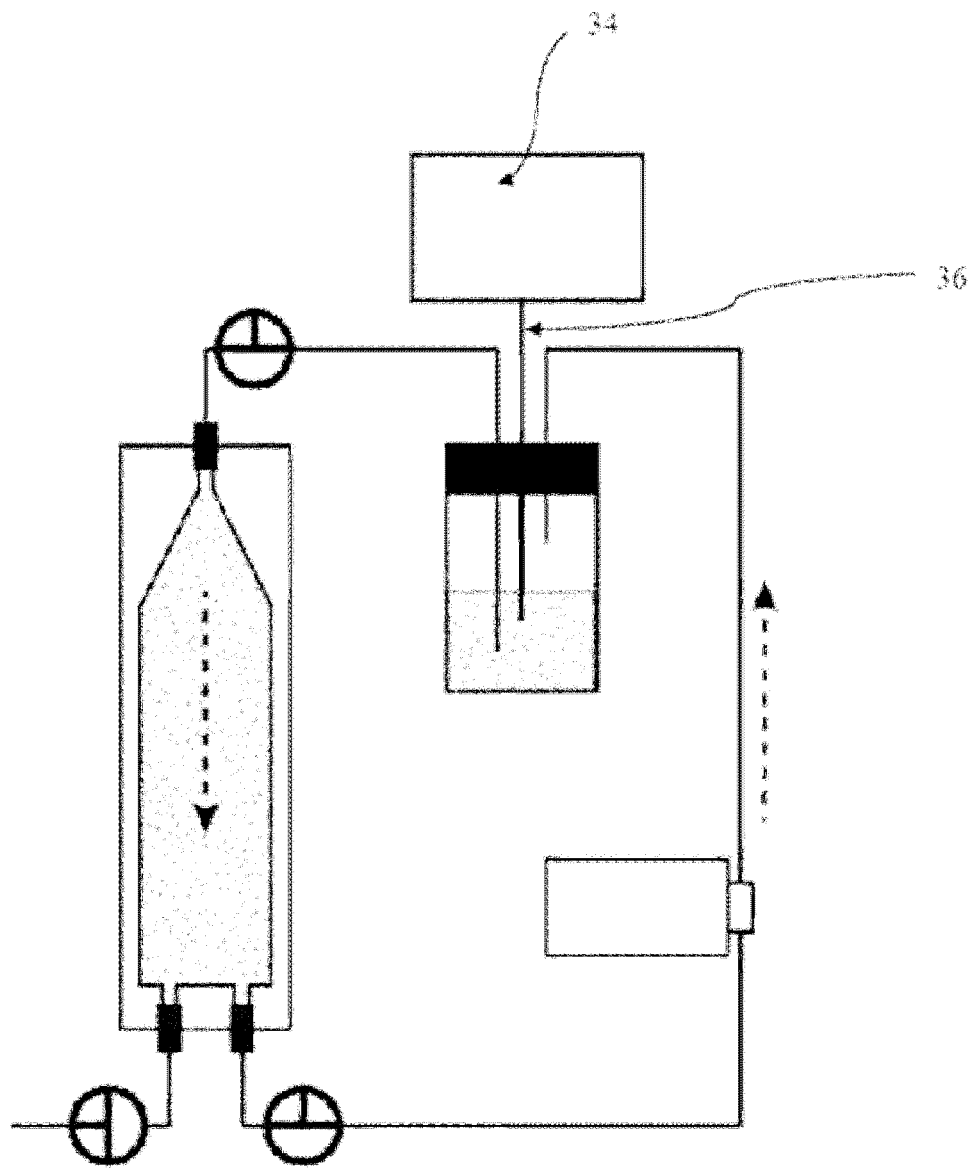
FIG. 3: A representation of a preferred embodiment of a system according to the invention with a gas source (34).

According to the embodiment of the system according to the invention represented in FIG. 3, a gas source (34) is provided, which is connected by a flow-through conduit (36) to the gas exchanger (26), in which a gas or a gas mixture is present, wherein the flow-through conduit (36) ends in the carrier fluid in the lower area of the gas exchanger. In another preferred embodiment, the gas source is connected by a flow-through conduit (36) to the upper part of the gas exchanger (26). The gas source (34) is preferably filled with the useful gas (28) which is needed for running the processes within the microfluidic droplets in the droplet incubator (10). The gas source (34) supplies the gas exchanger (26) with "fresh" useful gas (28) and thus allows an effective exchange of the gas or gas mixture within the gas exchanger (26). The gas source (34) can be filled, in particular, with gases or gas mixtures that are different from air or an ambient gas mixture.

Figure 4:
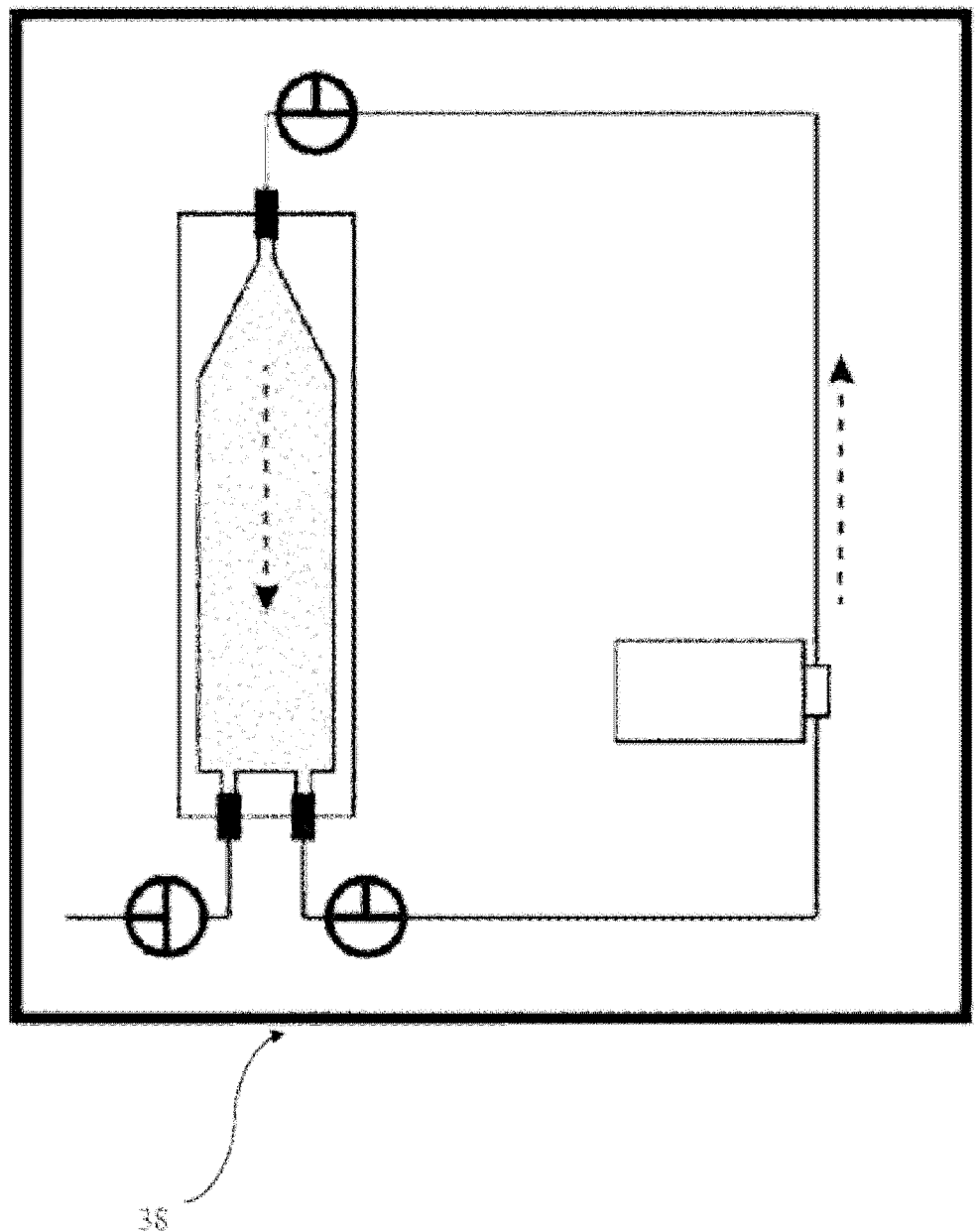
FIG. 4: A representation of a preferred embodiment of a system according to the invention with a housing (38).

FIG. 4 shows the preferred embodiment of the system according to embodiments of the invention according to FIG. 1, wherein, in addition to the structure shown in FIG. 1, the system is arranged in a closed housing (38). As shown in the description of FIG. 1, the uptake of the useful gas (28) by the carrier fluid (12) occurs through the gas-permeable material of the flow-through conduit (20). Since the embodiment according to FIG. 1 is arranged in a gas-tight housing (38) which can be filled with an application-determined gas or gas mixture, the uptake of the desired useful gas (28) through the gas-permeable material of the flow-through conduit (20) becomes possible. Thus, it is possible to dispense with a gas exchanger (26) as additional component within the closed circuit of the system according to embodiments of the invention, while nevertheless providing a useful gas (28) that is different from air.

Figure 5:
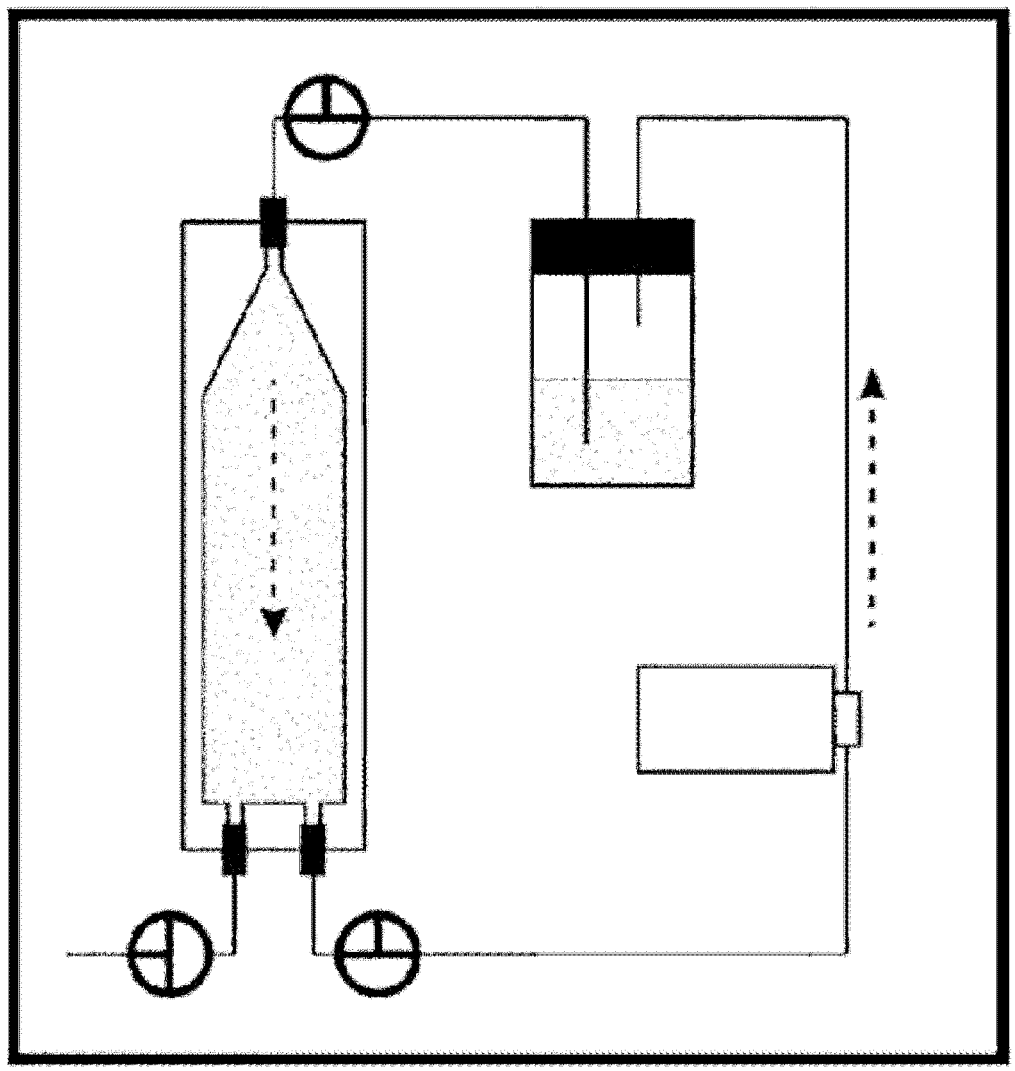
FIG. 5: A representation of a further preferred embodiment of a system according to the invention with a housing (38).

FIG. 5 shows an embodiment of the system according to the invention shown in FIG. 2, comprising additionally a gas-tight housing (38).

In the preferred embodiment shown in FIG. 6, the carrier fluid (12) is conveyed by a flow-through conduit (20) in the direction of the droplet incubator (10), wherein the propulsion of the flow is provided by the conveyor (22). In the embodiment of the invention shown in FIG. 6, the system according to embodiments of the invention consisting of droplet incubator (10), flow-through conduit (20) and gas exchanger (26) and conveyor (22) does not form a closed circuit for the carrier fluid (12). Instead, in the large container (40) of the gas exchanger (26), a large amount of the carrier fluid (12) is provided, which flows once through the droplet incubator in flow direction (14). Through the outlet (16c) of the lower part (10a) of the droplet incubator (10), the carrier fluid (12) which has passed through the droplet incubator (10) is fed to an additional use. This mode of operation of the system according to embodiments of the invention is preferably designed so that the large container (40) is arranged above the droplet incubator (10) and the carrier fluid (12) arrives in the droplet incubator (10) only as a result of the positional or potential energy which the carrier fluid (12) has available due to its arrangement of the large container (40) relative to the droplet incubator (10). In the case of this special arrangement which is not shown it is possible to dispense with a conveyor (22).

The following examples to which the corresponding data is presented in FIGS. 8-12 disclose experimental data obtained using a preferred system according to embodiments of the invention that has been used to incubate millions of droplets with a volume in the picoliter range (picoliter droplets) simultaneously for a controlled oxygen transfer and enhanced gas transfer. The improvement of the preferred system in comparison to systems of the prior art is demonstrated by measuring the oxygen concentration inside droplets. Herein the preferred embodiment of the system according to embodiments of the invention is denoted as a dynamic droplet incubation (DDI), while systems known from the prior art that are standard off-chip droplet incubations are denoted as static droplet incubation (SDI). It is noted that the expression droplets were dynamically incubated and the like equally refer to the use of a preferred system according to embodiments of the invention, while the expression droplets were incubated statically and similar expression refer to SDI mimicking systems and incubations methods known from the prior art. An important difference between DDI and SDI is, that in SDI the carrier fluid preferably an oil is not circulated. The experimental data show that DDI in comparison to SDI increases the oxygen transfer, which yields a dramatic increase in biomass and recombinant protein expression, wherein DDI reaches levels similar to a cultivation of cells in free solution as opposed to droplets in microtiter plates (MTPs) and shaking flasks. Moreover inter-droplet variations, in particular with respect to the oxygen concentration inside the droplet, are reduced in DDI compared to SDI.

Example 1: Working Principle of Dynamic Droplet Incubation

During dynamic droplet incubation (DDI) a constant top-to-bottom flow of perfluorinated oil through the densely packed droplet population in the incubation device is applied. In response to the interplay of drag and buoyancy, droplets are mixed, while retained in the incubator. Furthermore, the average inter-droplet distance is increased, which is observed by an expanded volume fraction occupied by the bulk of droplets. Contrasting to DDI and as a negative control mimicking current standard off-chip droplet incubation approaches, the device also allows storage of emulsions without oil circulation—in the following referred to as static droplet incubation (SDI).

Example 2: Dynamic Droplet Incubation Increases the Oxygen Transfer Rate

To estimate the influence of DDI and SDI on oxygen transfer into droplets, the dissolved oxygen concentration (DO) inside picoliter droplets during cell cultivation was monitored. Two distinct droplet populations, incubated either dynamically or statically, were generated from the same *E. coli* preculture to ensure equal initial oxygen consumption rates. Both droplet populations were inoculated at high cell densities (optical density (OD) 1≈170 cells/droplet) to allow for similar initial oxygen consumption rates amongst all droplets.

For SDI, the lower DO detection limit was reached within 17 minutes, indicating that the oxygen transfer rate was much lower than the initial bacterial oxygen uptake rate. On the contrary, droplets incubated dynamically showed only a mild decline in dissolved oxygen, indicating a higher oxygen transfer rate in comparison to SDI. Since cell replication gradually increases the oxygen uptake rate, DDI also reached the lower detection limit, but only after 100 min. However, superior oxygen transfer is subsequently maintained with DDI.

Using the dynamic method and the recirculation flow rate of 130 µL/min, the oxygen transfer rate (OTR) of the system was estimated to 5.5 mmol/L/h. With increased oil flow rates, the OTR reached nearly 20 mmol/L/h, reaching the order of magnitude reported for MTPs or shake flasks.

Example 3: Dynamic Droplet Incubation Enhances Cell Growth

The benefits of an enhanced oxygen transfer using a preferred system according to embodiments of the invention was further demonstrated by quantifying the biomass production of different microorganisms in droplets. To compare DDI and SDI, droplet populations with a total of $5 \times 10^6$ droplets were generated with the same cell or spore density. The biomass yield was evaluated after 24 h incubation. Both *B. subtilis* and the aerobic bacterium *P. fluorescens* exhibited growth only under DDI, evidencing the disadvantages of SDI and concomitant low oxygen availability. Moreover, the enhanced oxygen availability during DDI resulted in significantly higher biomass production of all microorganisms, with yields three to eleven times higher than in statically incubated droplets and remarkably similar to those obtained with standard microbial cultivation methods. These findings are supported by a further experiment, in which we monitored cell density of *E. coli* over time in picoliter droplets, MTPs and shaking flasks. While cell densities in dynamically incubated droplets, MTPs and shaking flasks reached similar levels after 24 h (~$OD_{600}$ 30), growth did not exceed ~$OD_{600}$ 5 with static incubation. Thus, we conclude that dynamic incubation allows oxygen supply in droplets comparable to that in commonly applied cultivation and screening platforms.

Example 4: Dynamic Droplet Incubation Enhances Protein Yields

Improved oxygen transfer and homogeneity through DDI is also reflected in the expression of heterologous proteins, which is of fundamental interest for most screening applications with biotechnological background. Therefore, the expression of the fluorescent reporter protein mCherry by *E. coli* cells encapsulated in droplets was investigated. To this end the emission intensity per droplet after 24 h of DDI and SDI, as well as for droplets that were generated from MTP and shaking flask cultures, was measured. The average fluorescence signal after dynamic incubation was 130-fold higher than the signal obtained after static incubation. Moreover, the fluorescence signal of dynamically incubated droplets reached similar intensities as droplets generated from MTP and shaking flask. The markedly reduced coefficient of variation for dynamically incubated droplets is in line with the superior homogeneity of oxygen availability during DDI compared to SDI. In a second experiment, it was confirmed that DDI also leads to an enhanced total yield of other recombinant proteins, in this case a camelid antibody fragment, independent of improved maturation.

Example 5: Dynamic Droplet Incubation Ensures Homogeneous Oxygen Availability To compare the homogeneity of oxygen transfer during DDI and SDI, incubated droplet populations were continuously re-injected and analyzed for biomass. The droplets were sequentially grouped into fractions reflecting their position in the incubator. For each fraction, statistic descriptors were calculated to assess differences within a droplet population. The fractions of the dynamically incubated population revealed high biomass yields at low variations, while on average lower yields and considerably higher variations were observed for SDI. The average biomass and corresponding standard deviation of the SDI fractions correlated with their position on the vertical axis of the incubator: The uppermost fraction and the lowest fractions in the incubator showed a significantly higher average in biomass with pronounced deviations among the droplets compared to the middle fractions. This inhomogeneity could be explained by the increased oxygen availability at the boundaries between droplet bulk and perfluorinated oil. DDI improves the homogeneity of oxygen distribution compared to SDI, since continuous mixing eliminates such boundary effects.

General Discussion of the Examples 1-5

The experimental data discussed in the Examples 1-5 are shown in FIGS. 8-12. This data demonstrates that the dynamic droplet incubation by using a system according to embodiments of the invention or preferred embodiments thereof allows for an improvement for the incubation in particularly for cells. In the prior art it has been described that droplets are statically stored in a variety of vessels, such as reaction tubes, syringes or droplet-holding chips, among others. These approaches however lack reproducibility and suffer from poor handling properties and/or throughput limitations. These drawbacks are exacerbated when droplets are used for cell-based assays, where static incubation methods known from the prior art provide inadequate oxygen availability. Oxygen availability drastically affects the physiological state of cells. Their genotypic distinctiveness is likely to be perturbed by phenotypic noise if oxygen cannot be provided sufficiently and homogeneously among all samples. In most cell-based applications, droplets are incubated as a non-agitated bulk denoted herein as statically incubated. In this case dissolved oxygen inside droplets is consumed within minutes as a consequence of cellular metabolic activity and is only replenished by diffusion from the boundaries of the droplet population towards the center of the emulsion. This process mainly takes place in the emulsion's aqueous phase (with lower diffusivity), thereby rapidly causing a gradient of dissolved oxygen across the bulk of droplets as well as low oxygen availability for droplets located in the center of the bulk. As presented herein, the dynamic droplet incubation as a method allows enhanced and homogeneous oxygen transfer during mid and long-term incubation of an entire picoliter droplet population. This strategy maintains flexibility in droplet volume and is not limited to the number of incubated droplets. Using bacteria and yeasts with biotechnological relevance, DDI resulted in higher biomass production with minimized inter-droplet variation with respect to the produced biomass. Moreover cell growth and recombinant protein production in droplets that have been incubated using DDI are similar to larger-scaled standard cultivation devices as MTPs and shaking flasks. This was a complete surprise and demonstrates the superiority of the system and method according to this invention in comparison to static droplet incubation known from the prior art. Moreover, DDI allows droplet incubation during extensive time periods, with minimal emulsion failure and low evaporation. As an integrative part of the microfluidic flow path, the incubation system presented herein supports implementation of gapless assay protocols, avoiding manual droplet recovery from external vessels and ultimately facilitating process automation. It is additionally possible to implement a control loop into the system that continuously modifies the oil recirculation rate dependent on a desired oxygen level, a process used in regular large scale fermentations. Moreover DDI can alternatively be implemented with gas mixtures other than air, e.g. using nitrogen for the cultivation of anaerobic bacteria or 5% carbon dioxide for the propagation of mammalian cells. Therefore, droplet-based screening platforms known from the prior art can be complemented with control over gas transfer using a system and/or a method according to embodiments of the invention or preferred embodiments thereof. This controlled gas transfer has not been addressed previously even though it constitutes a highly relevant aspect in numerous droplet applications. Moreover the incubation of droplets using the system and/or the method according to the invention showed similar cultivation success e.g. in terms of growth rates of the cells encapsulated in droplets in comparison to established experimentation techniques for cell cultivation in free solutions using MTPs and flasks. The cultivation in droplets however depicts tremendous advantages over cell cultivations in MTPs or flasks, since it allows for an efficient control of millions droplets that may serve as micro-reactors. The ease of use of the presented method and system therefore allows to establish novel assay miniaturizations, with culturing conditions that have previously only been possible with MTPs or flask, lacking the high throughput potential of the droplet technology.

It should be understood that various alternatives to the embodiments of the invention described herein may be employed in practicing the invention. It is intended that the claims define the scope of the invention and that the method and apparatus within the scope of these claims and their equivalents be covered thereby.

LIST OF REFERENCE NUMBERS

10 Droplet incubator
10a Cylindrical lower part of the droplet incubator
10b Conical upper part of the droplet incubator
12 Carrier fluid
14 Flow direction
16ab, b, c Fittings
18a, b, c Valve
20 Flow-through conduit
22 Conveyor
24 Connection to an additional test assembly
26 Gas exchanger
28 Useful gas
30 Reservoir
32 Cover and passage for flow-through conduit
34 Gas source
36 Flow-through conduit for the connection of the gas source to the gas exchanger
38 Housing or enclosure
40 Gas exchanger comprising a large reservoir with carrier fluid for exploiting the positional energy of the carrier fluid, arranged preferably above (not shown) the droplet incubator

What is claimed is:

1. System for incubating microfluidic droplets, the system comprising
   a droplet incubator,
   a flow-through conduit,
   a gas exchanger, and
   a pump,
   wherein the droplet incubator comprises a first container having a lower cylindrical part and an upper conical part configured for the incubation microfluidic droplets in a carrier fluid comprising a dissolved gas,
   wherein the carrier fluid is an oily carrier fluid,
   wherein said microfluidic droplets are aqueous droplets in the oily carrier fluid and comprise cell suspensions and/or dissolved reagents, wherein the droplet incubator is connected by the flow-through conduit to the gas exchanger, which is configured to allow for an exchange of gas between the carrier fluid and a gas source, the flow-through conduit forming a circuit that conducts the oily carrier fluid and wherein the pump leads the oily carrier fluid continuously through the flow-through conduit, the droplet incubator and the gas exchanger,
   wherein the gas exchanger comprises
   a second container, which is connected to the gas source and wherein a first part of the flow-through conduit connecting the second container to the upper part of the droplet incubator protrudes in a lower area of said second container, wherein the lower area of the second container contains the oily carrier fluid, and a second part of the flow-through conduit connecting the gas exchanger to the lower part of the droplet incubator protrudes in an upper area of the second container, wherein the upper area of the second container contains gas provided by the gas source, wherein the second container is partially filled with the oily carrier fluid and partially filled with gas provided by the gas source.

2. The system according to claim 1, wherein the second container is contained within a gas-tight enclosure, wherein an enclosed volume of the gas-tight enclosure forms gas reservoir of the gas exchanger.

3. The system according to claim 1, wherein the second container is in communication with an ambient atmosphere, and an air mixture is a component of the gas source and/or the second container is partially filled with gases and/or gas mixtures that are different from air, as gas source.

4. The system according to claim 1, wherein the system further comprises a gas sensor configured to determine a concentration of dissolved gases or gas mixtures.

5. The system according to claim 1, wherein the pump is configured to generate a cyclic and/or continuous flow of the closed circuit consisting of the droplet incubator, the gas exchanger and the flow-through conduit.

6. The system according to claim 1, wherein the system further comprises 10,000 to 10 billion microfluidic droplets.

7. The system according to claim 1, wherein the system further comprises a detector configured to determine the oxygen concentration within the microfluidic droplets and the system is configured such that the flow rate of the carrier fluid is adjusted by the pump according to the measured oxygen concentration.

8. A method for providing homogeneous incubation conditions in a droplet incubator by targeted introduction of gases or gas mixtures into a carrier fluid, the method comprising the following steps:

a) providing the system according to claim 1 comprising a droplet incubator, a gas exchanger and a conveyor, wherein in the droplet incubator, microfluidic droplets are present, which comprise cell suspensions and/or dissolved reagents, and the droplet incubator is connected by a flow-through conduit to a gas exchanger, wherein the flow-through conduit forms a circuit that conducts a carrier fluid which comprises gas or gas mixtures, b) generating a cyclic and/or continuous flow of the carrier fluid through the closed circuit formed by the flow-through conduit, a droplet incubator and a gas exchanger, b) exchanging at least a portion of the gases or gas mixtures dissolved in the carrier fluid during a residence time of the carrier fluid in the gas exchanger, and c) exchanging at least a portion of the gases or gas mixtures dissolved in the carrier fluid, during the flow of the carrier fluid through the droplet incubator.

9. The method according to claim 8, wherein the method comprises providing a carrier fluid with a plurality of microfluidic droplets in the droplet incubator.

10. The system according to claim 4, wherein the system further comprises dissolved gasses or gas mixtures that comprise oxygen.

11. The system according to claim 1, wherein the system further comprises 500,000 to 500 million microfluidic droplets.

12. The system according to claim 1, wherein the system further comprises 2 million to 20 million microfluidic droplets.

13. The system according to claim 1, wherein the system further comprises 3 million to 7 million microfluidic droplets.

14. The system according to claim 4, wherein the system comprises a regulator configured to regulate the concentration of dissolved gases or gas mixtures in the carrier fluid by adjusting the flow rate of the carrier fluid by the pump.

15. System for incubating microfluidic droplets, the system comprising
a droplet incubator,
a flow-through conduit, and
a pump,
wherein the droplet incubator comprises a container having a lower cylindrical part and an upper conical part configured for the incubation microfluidic droplets in a carrier fluid comprising a gas dissolved in the gas,
wherein the carrier fluid is an oily carrier fluid,
wherein said microfluidic droplets are aqueous droplets in the oily carrier fluid and comprise cell suspensions and/or dissolved reagents,
wherein the flow-through conduit forms a circuit that conducts the oily carrier fluid,
wherein the flow-through conduit is gas permeable, and
wherein the pump leads the oily carrier fluid continuously through the flow-through conduit and the droplet incubator.

16. The system according to claim 15, wherein the flow-through circuit is contained within a gas-tight enclosure, wherein an enclosed volume of the gas-tight enclosure forms a gas reservoir of the flow-through circuit.

17. The system according to claim 15, wherein the flow-through circuit is exposed to an ambient atmosphere of gases and/or gas mixtures that are different from air, as gas source.

18. The system according to claim 15, wherein the system further comprises a gas sensor configured to determine a concentration of dissolved gases or gas mixtures.

19. The system according to claim 15, wherein the pump is configured to generate a cyclic and/or continuous flow of the closed circuit consisting of the droplet incubator and the flow-through conduit.

20. The system according to claim 15, wherein the system further comprises 10,000 to 10 billion microfluidic droplets.

* * * * *

UNITED STATES PATENT AND TRADEMARK OFFICE
CERTIFICATE OF CORRECTION

PATENT NO.       : 10,745,660 B2
APPLICATION NO.  : 14/937197
DATED            : August 18, 2020
INVENTOR(S)      : Miguel Tovar et al.

Page 1 of 1

It is certified that error appears in the above-identified patent and that said Letters Patent is hereby corrected as shown below:

In the Claims

In Column 30, Line 42, Claim 2, delete "gas" and insert --a gas--.

In Column 31, Line 14, Claim 8, delete "b)" and insert --c)--.

In Column 31, Line 17, Claim 8, delete "c)" and insert --d)--.

Signed and Sealed this
Eighth Day of December, 2020

Andrei Iancu
*Director of the United States Patent and Trademark Office*